United States Patent [19]
Salyers et al.

[11] Patent Number: 5,322,784
[45] Date of Patent: Jun. 21, 1994

[54] **METHOD AND MATERIALS FOR INTRODUCING DNA INTO *PREVOTELLA RUMINICOLA***

[75] Inventors: Abigail A. Salyers; Nadja B. Shoemaker, both of Champaign; Mikeljon P. Nikolich, Urbana, all of Ill.

[73] Assignees: The Board of Trustees of the University of Illinois, Urbana-Champaign, Illinois, Urbana; Biotechnology Research and Development Corporation, Peoria, both of Ill.

[21] Appl. No.: 718,535

[22] Filed: Jun. 5, 1991

[51] Int. Cl.$^5$ .................. C12N 1/21; C12N 15/63; C12N 15/74

[52] U.S. Cl. ................. 435/172.3; 435/252.3; 435/320.1

[58] Field of Search ............... 435/172.3, 252.3, 320.1

[56] References Cited

PUBLICATIONS

Abraham, et al., *Plasmid*, 19:113–120 (1988).
Anderson, et al., "Development of Techniques for the Genetic Manipulation of *Bacteroides ruminicola*," Abstract, University of Illinois, Jun. 1990.
Burdett, *J. Bacteriol.*, 165:564–569 (1986).
Devereux, et al., *Nucl. Acids Res.*, 12:387–395 (1985).
DeVries, et al., *Proc. Nat. Acad. Sci. USA*, 57:1010–1012 (1967).
Flint, et al., *Appl. Environ. Microbiol.*, 54:855–860 (1988).
Guiney, et al., *J. Bacteriol.*, 172:495–497 (1990).
Henikoff, *Gene*, 28:351 (1984).
Jacquet, et al., *The EMBO J.*, 7:2861–2867 (1988).
Jurnak, *Science*, 230:32–36 (1985).
Lacks, et al., *J. Mol. Biol.*, 192:753–765 (1986).
LeBlanc, et al., *J. Bacteriol.*, 170:3618–3626 (1988).
Lederberg, et al., *J. Bacteriol.*, 119:1072–1074 (1974).
Manavathu, et al., *Antimicrob. Agents Chemother.*, 34:71–77 (1990).
Manavathu, et al., *Gene*, 62:17–26 (1988).
Martin, et al., *Nucl. Acids Res.*, 14:7047–7058 (1986).
Meyer, et al., *J. Bacteriol.*, 143:1362–1373 (1980).
Odelson, et al., *Plasmid*, 17:87–109 (1987).
Rigby, et al., *J. Mol. Biol.*, 113:237–251 (1977).
Salyers, et al., *CRC Critical Reviews in Microbiology*, 14:49–71 (1987).
Sancar, et al., *J. Bacteriol.*, 137:692–693 (1979).
Sanchez-Pescador, et al., *Nucl. Acids Res.*, 16:1216–1218 (1988).
Shah, et al., *Intl. J. Syst. Bacteriol.*, 40:205–208 (1990).
Shoemaker, et al., *Appl. Environ. Microbiol.*, 57:2114–2120 (1991).
Shoemaker, et al., *J. Bacteriol.*, 172:1694–1702 (1990).
Shoemaker, et al., *J. Bacteriol.*, 166:959–965 (1986).
Shoemaker, et al., *J. Bacteriol.*, 170:1651–1657 (1988).
Shoemaker, et al., *J. Bacteriol.*, 162:626–632 (1985).
Shoemaker, et al., *J. Bacteriol.*, 171:1294–1302 (1989).
Simon, et al., *Bio/Technology*, 1:784–791 (1983).
Smith, *J. Bacteriol.*, 169:4589–4596 (1987).
Smith, *J. Bacteriol.*, 164:294–301 (1985).
Sougakoff, et al., *FEMS Microbiol. Lett.*, 44:153–159 (1987).
Speer, et al., *J. Bacteriol.*, 170:1423–1429 (1988).
Stevens, et al., *J. Bacteriol.*, 172:4271–4279 (1990).
Thomson, et al., *FEMS Microbiol. Letters*, 61:101–104 (1989).
Thomson, et al., *Current Microbiology*, 24:49–54 (1992).
Valentine, et al., *J. Bacteriol.*, 170:1319–1324 (1988).
Whitehead, et al., *Appl. Environ. Microbiol.*, 55:893–896 (1989).

*Primary Examiner*—Richard A. Schwartz
*Assistant Examiner*—Philip W. Carter
*Attorney, Agent, or Firm*—Willian Brinks Olds Hofer Gilson & Lione

[57] ABSTRACT

A method of introducing expressible heterologous DNA into *Prevotella ruminicola* is provided. The method involves conjugal transfer of a shuttle vector comprising the heterologous DNA operatively linked to a promoter functional in *P. ruminicola*. The invention also provides shuttle vectors for use in the method and *P. ruminicola* produced by the method. The invention further provides a tetracycline resistance gene of the TetQ class, or fragments thereof that confer tetracycline resistance, and a protein of the TetQ class that provides resistance to tetracycline by protecting ribosomes from tetracycline, or active fragments thereof. Finally, the invention provides a promoter functional in *P. ruminicola* and an engineered *P. ruminicola* comprising expressible foreign DNA.

12 Claims, 10 Drawing Sheets

```
              0                      *                                                    49
Bat-TetQ    MNIINLGILA    HIDAGKTSVT    ENLLFASGAT    EKCGCVDNGD    TITDSMDIEK
Caj-TetO    MKIINLGILA    HVDAGKTTLT    ESLLYTSGAI    AELGSVDEGT    TRTDTMNLER
Stp-TetM    MKIINIGVLA    HVDAGKTTLT    ESLLYNSGAI    TELGSVDRGT    TKTDNTLLER
Consensus   MkIINlGiLA    HvDAGKTtlT    EsLLy.SGAi    .elGsVD.Gt    T.TD.m.lEr
              S + +       $ $+SS++ +      + +  +        + + +        +   +

50                     *                                                    99
Bat-TetQ    RRGITVRAST    TSIIWNGVKC    NIIDTPGHMD    FIAEVERTFK    HLDGAVLILS
Caj-TetO    QRGITIQTAV    TSFQWEDVKV    NIIDTPGHMD    FLAEVYRSLS    VLDGAVLLVS
Stp-TetM    QRGITIQTAI    TSFQWKNTKV    NIIDTPGHMD    FLAEVYRSLS    VLDGAILLIS
Consensus   qRGITiqta.    TSfqW..vKv    NIIDTPGHMD    FlAEVyRsls    vLDGAVLl.S
             S+$$$             +        +++S+$$$ $     + ++ ++        ++$+$ 100                             *        *                                  149
Bat-TetQ    AKEGIQAQTK    LLFNTLQKLQ    IPTIIFINKI    DRAGVNLERL    YLDIKANLSQ
Caj-TetO    AKDGIQAQTR    ILFHALQIMK    IPTIFFINKI    DQEGIDLPMV    YREMKAKLSS
Stp-TetM    AKDGVQAQTR    ILFHALRKIG    IPTIFFINKI    DQNGIDLSTV    YQDIKEKLSA
Consensus   AKdGiQAQTr    iLFhaLqk..    IPTIfFINKI    Dq.GidL...v   Y.diKakLS.
              $     $                   + + + SS      S   +                +

150                                                                         199
Bat-TetQ    DVLFMQNVVD    GSVYPVCSQT    YIKEEYKEFV    CNHDDNILER    YLADSEISPA
Caj-TetO    EIIVKQKVGQ    HPHINVTDND    DMEQ..WDAV    IMGNDELLEK    YMSGKPFKMS
Stp-TetM    EIVIKQKVEL    HPNMRVMNFT    ESEQ..WDMV    IEGNDYLLEK    Y.TSGKLLEAL
Consensus   ei..kQkV..    hp...V...t    ..eq..wd.V    i.gnD.lLEk    Y.sgk.....
                 +                                      ++           + +

200                                                                         249
Bat-TetQ    DYWNTIIALV    AKAKVYPVLH    GSAMFNIGIN    ELLDAITS.F    ILPPASVSNR
Caj-TetO    ELEQEENRRF    QNGTLFPVYH    GSAKNNLGTR    QLIEVIASKF    YSSTPEGQSE
Stp-TetM    ELEQEESIRF    HNCSLFPVYH    GSAKNNIGID    NLIEVITNKF    YSSTHRGQSE
Consensus   eleqee..rf    .n..lfPVyH    GSAknNiGi.    .LievItskF    ysst..gqse
              +                          ++          +++  + +

250                                                                         299
Bat-TetQ    LSSYLYKIEH    DPKGHKRSFL    KIIDGSLRLR    DVVRINDSEK    FIKIKNLKTI
Caj-TetO    LCGQVFKIEY    SEKRRRFVYV    RIYSGTLHLR    DVIRISEKEK    .IKITEMYVP
Stp-TetM    LCGKVFKIEY    SEKRQRLAYI    RLYSGVLHLR    DPVRISEKEK    .IKITEMYTS
Consensus   Lcg.vfKIEy    seKr.r..y.    riysG.LhLR    DvvRIsekEK    .IKItemyt.
               +++                      $ ++$ +          +

300                                                                         349
Bat-TetQ    NQGREINVDE    VGANDIAIVE    DMDDFRIGNY    LGAEPCLIQG    ..LSHQHPAL
Caj-TetO    TNGELYSSDT    ACSGDIVILP    N.DVLQLNSI    LGNEILLPQR    KFIENPLPMI
Stp-TetM    INGELCKIDK    AYSGEIVILQ    N.EFLKLNSV    LGDTKLLPQR    ERIENPLPLL
Consensus   .nGel...D.    a.sgdIvll.    n.d.l.lns.   LG.e.lLpQr    ..ienplP.l
                            +                          +              + +
```

FIGURE 6A

|  | 350 |  |  |  | 399 |
|---|---|---|---|---|---|
| Bat-TetQ | KSSVRPDRPE | ERSKVISALN | TLWIEDPSLS | FSINSYSDEL | EISLYGLTQK |
| Caj-TetO | QTTIAVKKSE | QREILLGALT | EISDCDPLLK | YYVDTTTHEI | ILSFLGNVQM |
| Stp-TetM | QTTVEPSKPQ | QREMLLDALL | EISDSDPLLR | YYVDSATHEI | ILSFLGKVQM |
| Consensus | qttv.p.kpe | qRe.ll.AL. | eisd.DPlL. | yyvds.thEi | ilSflG.vQm |
|  |  | + ++ | ++ |  | + |

|  | 400 |  |  |  | 449 |
|---|---|---|---|---|---|
| Bat-TetQ | EIIQTLLEER | FSVKVHFDEI | KTIYKERPVK | KVNKIIQIEV | PPNPYWATIG |
| Caj-TetO | EVICAILEEK | YHVEAEIKEP | TVIYMERPLR | KAEYTIHIEV | PPNPFWASVG |
| Stp-TetM | EVTCALLQEK | YHVEIEIKEP | TVIYMERPLK | KAEYTIHIEV | PPNPFWASIG |
| Consensus | EvicalLeEk | yhVe.eikEp | tvIYmERPlk | KaeytIhIEV | PPNPfWAsiG |
|  |  | + + | + + + |  |  |

|  | 450 |  |  |  | 499 |
|---|---|---|---|---|---|
| Bat-TetQ | LTLEPLPLGT | GLQIESDISY | GYLNHSFQNA | VFEGIRMSCQ | SGLHGWEVTD |
| Caj-TetO | LSIEPLPIGS | GVQYESRVSL | GYLNQSFQNA | VMEGVLYGCE | QGLYGWKVTD |
| Stp-TetM | LSVAPLPLGS | GVQYESSVSL | GYLNQSFQNA | VMEGIRYGCE | QGLYGWNVTD |
| Consensus | Ls.ePLPlGs | GvQyES.vSl | GYLNqSFQNA | VmEGirygCe | qGLyGW.VTD |
|  | + + | + | + | + + | ++ + |

|  | 500 |  |  |  | 549 |
|---|---|---|---|---|---|
| Bat-TetQ | LKVTFTQAEY | YSPVSTPADF | RQLTPYVFRL | ALQQSGVDIL | EPMLYFELQI |
| Caj-TetO | CKICFEYGLY | YSPVSTPADF | RLLSPIVLEQ | ALKKAGTELL | EPYLHFEIYA |
| Stp-TetM | CKICFKYGLY | YSPVSTPADF | RMLAPIVLEQ | VLKKAGTELL | EPYLSFKIYA |
| Consensus | cKicF.yglY | YSPVSTPADF | R.L.PiVleq | aLkkaGtelL | EPyL.Feiya |
|  | + ++ | + + |  | + + | ++ |

|  | 550 |  |  |  | 599 |
|---|---|---|---|---|---|
| Bat-TetQ | PQAASSKAIT | DLQKMMSEIE | DISCNNEWCH | IKGKVPLNTS | KDYASEVSSY |
| Caj-TetO | PQEYLSRAYH | DAPRYCADIV | STQIKNDEVI | LKGEIPARCI | QEYRTDLTYF |
| Stp-TetM | PQEYLSRAYN | DAPKYCANIV | DTQLKNNEVI | LSGEIPARCI | QEYRSDLTFF |
| Consensus | PQeylSrAy. | Dapkyca.Iv | dtq.kN.evi | lkGeiParci | qeYrsdlt.f |
|  | + |  | + + | + | + |

|  | 600 |  |  |  | 645 |
|---|---|---|---|---|---|
| Bat-TetQ | TKGLGIFMVK | PCGYQITKGG | YSDNIRMNEK | ..DKLLFMFQ | KSMSSK |
| Caj-TetO | TNGQGVCLTE | LKGYQPAIGK | FICQPRRPNS | RIDKVRHMFT | S |
| Stp-TetM | TNGRSVCLTE | LKGYHVTTGE | PVCQPRRPNS | RIDKVRYMFN | KIT |
| Consensus | TnG.gvclte | lkGYq.t.G. | ..cqpRrpns | riDKvr.MF. | k |
|  | + + | + |  |  |  |

```
                    2Δ1
                   (R/R)
                    |
tetQ    1   CTCAAATGCCAAACTAAAGAAGATATTGGCCAAAATAAACGCTATACCGAGAGAGAAACT    60 tetQ   61   TGATTTTTCAACTTCCTAAAAACAGTGTTGTTCAAACATTTCTACTTATTGTACTTACCA   120

2Δ2
                                           (R/I)
                                            |
tetQ  121   GTTGAACCTACGTTTCCCTAATAAAATGTCTATGGTAAAAAGTTAAAAAATCCTCCTACT   180
tetO        ttgcactttattataggg gcttagttttttgtac
tetM        atgtcctttttaggaggg gcttagttttttgtac tetQ  181   TTTGTTAGATATATTTTTTGTGTAATTTTGTAATCGTTATGCGGGCAGTAATAATATACA   240
tetO        ccagtttaagaatacttttatcatgtaATTtTA...TATgCccgaaaAcA.TATaaGt.T
tetM        ccagtttaagaataccttatcatgtgATTcTAaagTATcCCcg....AcAaTATctGtaT
```

FIGURE 7B

```
                                                                              2Δ3
                                                                             (R/S)
                                                                              |
         +         +         +         +         +         +         +
tetQ     TATTAATACGAGTTATTATTAATCCTGTGTAGTTCTCATATGCTACGAGGAGTATTAAAAGGTG
    241
tetO GtTTTT.ggggCtatTGGagTTATtca......CCCAgtGATAggAGTATTTATCACTGG
300
tetM GcTTTgtatgCctaTGG..TTATgcataaaatCCCAgtGATAagAGTATTTATCACTGG 2Δ5                    2Δ6
                                             (S/S)                  (S/S)
                                              |                      | MetAsnIleIleAsn>
                                       2Δ4       -10
                                      (I/S)      ___
                                        |
         +         +         +         +         +         +         +
tetQ     CGTTTCGACAATGCATCTATTGTAGTATATTATTGCTTAATCCAAATGAATATTATAAAT
    301  ___
          -35
tetO GtATTTTATGCCCt.tTTTTGGG.TgTTGAtaGGAggGAAAATCACATG
360
tetM G.ATTTTATGCCCC..TTTTGGGtTtTTGAatGGAggGAAAATCACATG
```

METHOD AND MATERIALS FOR INTRODUCING DNA INTO *PREVOTELLA RUMINICOLA*

This invention was made with government support provided by Grant No. 59 32U4-7-119 awarded by the United States Department of Agriculture. The government has certain rights in the invention.

FIELD OF THE INVENTION

This invention relates generally to methods and materials for the genetic manipulation of *Prevotella ruminicola*. This invention also relates to a novel class of tetracycline resistance genes.

BACKGROUND OF THE INVENTION

A. Bacteroides and Prevotella

Bacteroides is a genus of Gram negative, obligately anaerobic bacteria found in the gastrointestinal tracts of humans and animals. These bacteria function in metabolizing a wide range of carbohydrates. In humans, Bacteroides account for approximately 25% of the bacteria in the colon.

*Prevotella ruminicola* is a species of Gram negative, obligately anaerobic bacteria found in the rumen of cattle. *P. ruminicola* ferment carbohydrates such as hemicellulose, cellobiose, and starch and aid digestion and degradation of polysaccharides. *P. ruminicola* was previously classified as a member of the genus Bacteroides (*Bacteroides ruminicola*) because it has some characteristics associated with human colonic Bacteroides However, recent investigations showed that *P. ruminicola* shared less than 5% DNA-DNA homology with the colonic Bacteroides species. More detailed biochemical analyses also suggested that it belonged in a separate genus, Prevotella [See Shah, et al., *Intl. J. Syst. Bacteriol.*, 40:205-208 (1990)].

Some progress has been made in connection with genetic manipulation of obligately anaerobic Bacteroides from the human colon. For example, shuttle vectors have been developed for use with some colonic Bacteroides which contain DNA from cryptic Bacteroides plasmids which are able to replicate in a number of different Bacteroides species [See Odelson, et al., *Plasmid*, 17:87-109 (1987); Salyers, et al., *Crit. Rev. Microbiol.*, 14:49-71 (1987); Valentine, et al., *J. Bacteriol.*. 170:1319-1324 (1988)]. These vectors also contain sequences which allow them to replicate in *E. coli* and be mobilized out of *E. coli* by IncP plasmids. The IncP plasmids R751 and RP4 have been shown to mobilize DNA from *E. coli* to a variety of other species, including colonic Bacteroides species [See Salyers, et al., *Crit. Rev. Microbiol.*, 14:49-71 (1987); Shoemaker, et al., *J. Bacteriol.*, 166:959-965 (1986)]. One such *E. coli*-Bacteroides shuttle vector is pVAL-1 which contains cryptic Bacteroides plasmid pB8-51 [Valentine, et al., *J. Bacteriol.*, 170:1319-1324 (1988)].

Certain colonic Bacteroides strains have been found to harbor large self-transmissible elements carrying a tetracycline resistance ("Tc$^r$") gene which are referred to as "conjugal elements" or "Tc$^r$ elements." Some of these Tc$^r$ elements also carry a clindamycin-erythromycin resistance ("Em$^r$") gene and are referred to as "Tc$^r$Em$^r$ elements." These elements are not plasmids, but are integrated into the host chromosome.

The Tc$^r$ and Em$^r$ genes from a conjugal Tc$^r$Em$^r$ strain of Bacteroides, *Bacteroides thetaiotaomicron* DOT, have been cloned, along with regions of the element that include transfer genes [Shoemaker, et al., *J. Bacteriol.*, 171:1294-1302 (1989)]. The Tc$^r$Em$^r$ element from *B. thetaiotaomicron* DOT has been designated "Tc$^r$Em$^r$-DOT."

These conjugal elements are able to transfer themselves from one colonic Bacteroides strain to another and to mobilize co-resident plasmids, not only from Bacteroides to Bacteroides, but also from Bacteroides to *E. coli* [See Odelson, et al., *Plasmid*, 17:87-109 (1987); Salyers, et al., *Crit. Rev. Microbiol.*, 14:49-71 (1987); Thomson, et al., *FEMS Microbiol. Letters*, 61:101-104 (1989); Stevens, et al., *J. Bacteriol.* 172:4271-4279 (1990)]. Thus, the Tc$^r$ and Tc$^r$Em$^r$ conjugal elements found in the colonic Bacteroides strains appear to be able to mediate mating pair formation between diverse genera of bacteria.

The conjugal element, Tc$^r$Em$^r$ 12256, has been found to mobilize co-resident plasmids at high frequencies [See Valentine, et al., *J. Bacteriol.*, 170:1319-1324 (1988)]. Furthermore, the Tc$^r$Em$^r$ 12256 element appears to exhibit constitutive transfer, as opposed to other Tc$^r$ and Tc$^r$Em$^r$ elements which require pre exposure to tetracycline to obtain maximum transfer frequencies.

Plasmid DNA has been introduced into some colonic Bacteroides using transformation techniques [See Salyers, et al., *CRC Clinical Reviews in Microbiology*, 14:49-71 (1987); Odelson, et al., *Plasmid* 17:87-109 (1987); Smith, *J. Bacteriol.*, 164:294-301 (1985)]. For instance, one colonic Bacteroides species has been transformed by electroporation [Thomson, et al., *FEMS Microbiol. Letters*. 61:101-104 (1989)]. An *E coli*-colonic Bacteroides shuttle vector, pDP1, was isolated from *Bacteroides uniformis* and electroporated into *B. uniformis* at a frequency of $10^6$ transporants per microgram of DNA. However, the same plasmid, when isolated from *E. coli* EM24, gave only $10^3$ transporants per microgram of DNA.

Standard methods, however, appear to be inadequate in several respects for the transformation of the colonic Bacteroides. For example, large plasmids are difficult to introduce into these species by transformation techniques. Best results are obtained when the plasmid DNA is less that 5 kbp in size. Also, to obtain good rates of transformation, the donor plasmid must be isolated from the same strain used as the recipient. The difficulties encountered in crossing species lines are believed to be due to the presence of restriction barriers. Also, successful transformation of many species of colonic Bacteroides has been sporadic [See Odelson, et al., *Plasmid*, 17:102 (1987)]. Clearly, much improvement is needed in transformation methods for colonic Bacteroides.

Despite progress in understanding the genetics of colonic Bacteroides, *P. ruminicola* is not well understood genetically. There have been some biochemical studies of polysaccharide utilization by *P. ruminicola*, and a xylanase gene from *P. ruminicola* has been cloned and expressed in *E. coli* [See Whitehead, et al., *Appl. Eviron. Microbiol.*, 55:893-896 (1989)].

Recently, a naturally-occurring plasmid carrying a gene coding for tetracycline resistance has been identified ("pRRI4") in *P. ruminicola* 223/M2/7. The pRRI4 plasmid was shown to transfer from *P. ruminicola* 223/M2/7 into *P. ruminicola* F101, but not into *P. ruminicola* 23, by conjugation [Flint, et al., *Appl. Environ. Microbiol.*, 54:855-860 (1988)].

It has also been reported that the pRRI4 plasmid can be introduced into *P. ruminicola* F101 by electroporation, but not into *P. ruminicola* 118B, M384, GA33 by this method [Thomson and Flint, *FEMS Microbiol. Letters*, 61:101-104 (1989)]. This article also reports that pRRI4 isolated from *P. ruminicola* could not be introduced into *B. uniformis*, a colonic Bacteroides, by electroporation. Thomson and Flint also discloses that the *E. coli*-colonic Bacteroides shuttle vector pDPI could not be introduced into *P. ruminicola* by electroporation. This was true whether pDPI was extracted from *B. uniformis* or *E. coli*.

From the above discussion, it is clear that, prior to the present invention, the genetic manipulation of *P. ruminicola* was not possible. Little was known about the genetics of *P. ruminicola*, making the use of vectors that could be manipulated and amplified in a known host, such as *E. coli*, highly desirable However, no shuttle vectors were known that could be used in *P. ruminicola*. Transformation and conjugal transfer of pRRI4 was possible, but pRRI4 cannot be used as a shuttle vector due to its relatively large size (19.5 kbp) and its inability to replicate in *E. coli*.

B. Tetracycline Resistance

Many bacteria, including strains of Bacteroides and Prevotella, possess tetracycline resistance genes. Three types of tetracycline resistance have been described and subdivided into classes defined by DNA-DNA hybridization.

The first type, tetracycline efflux, is mediated by a 40-50 kDa membrane protein which transports tetracycline out of the cell. Examples of this mode of resistance have been found in Gram-negative enterics [classes TetA-G; Aoki, *Micro. Sci.*, 5:219-223 (1988); Levy, *ASM News*, 54:418-421 (1988)] and some Gram-positive bacteria [classes TetK and TetL; Lacks, et al., *J. Mol. Biol.*, 192:753-765 (1986); McMurry, et al., *Antimicrob. Agents Chemother.*, 32:1646-1650 (1987)].

The second type of tetracycline resistance, ribosome protection, is mediated by a 72-75 kDa cytoplasmic protein which interacts with ribosomes and prevents inhibitory binding of tetracycline. Examples of this mode of resistance have been found in many Gram-positive and some Gram-negative bacteria [classes TetM and TetO; Burdett, *J. Bacteriol.*, 165:564-569 (1986); Manavathu, et al., *Gene*, 62:17-26 (1988); Sougakoff, et al., *FEMS Microbiol. Lett.*, 44:153-159 (1987)].

The third type of resistance, tetracycline modification, is mediated by a 44 kDa cytoplasmic protein which chemically inactivates tetracycline. The only known representative of this mode of resistance, class TetX, was orginally found in *B. fragilis* [Speer and Salyers, *J. Bacteriol.*, 170:1423-1429 (1988)].

Two other $Tc^r$ genes are known. TetN is an unsequenced streptococcal $Tc^r$ which is reported to confer ribosome protection type resistance [Burdett, *J. Bacteriol*, 165:564-569 (1986)]. TetP is an uncharacterized $Tc^r$ determinant from *Clostridium prefringens* [Abraham, et al., *Plasmid*, 19:113-120 (1988)].

SUMMARY OF THE INVENTION

The invention provides for the first time a method for the genetic manipulation of *Prevotella ruminicola*. In particular, the present invention provides a method for introducing heterologous DNA into *P. ruminicola*. The method comprises transforming *E. coli* with a shuttle vector comprising: a mobilization region which permits transfer of the shuttle vector from *E. coli* to a colonic Bacteroides species; a mobilization region which permits transfer of the shuttle vector from the colonic Bacteroides species to a *P. ruminicola:* and heterologous DNA operatively linked to a promoter functional in *P. ruminicola*. After transformation of the *E. coli* with the shuttle vector, the *E. coli* is contacted with the colonic Bacteroides species under conditions sufficient so that the shuttle vector is transferred from the *E. coli* to the colonic Bacteroides species. Finally, the colonic Bacteroides species containing the shuttle vector is contacted with the *P. ruminicola* under conditions sufficient so that the shuttle vector is transferred from the colonic Bacteroides species to the *P. ruminicola*.

The invention also comprises *P. ruminicola* produced by this method and a shuttle vector useful for transferring heterologous DNA to *P. ruminicola* by conjugation. The shuttle vector comprises: a mobilization region which permits transfer of the shuttle vector from *E. coli* to a colonic Bacteroides species; a mobilization region which permits transfer of the shuttle vector from the colonic Bacteroides species to a *P. ruminicola;* and heterologous DNA operatively linked to a promoter functional in the *P. ruminicola*. These shuttle vectors are particularly advantageous because they can be amplified and manipulated in *E. coli* before they are used to introduce heterologous DNA into *P. ruminicola*.

The invention further provides a tetracycline resistance gene of the TetQ class, or fragments thereof, that confer tetracycline resistance. The TetQ class is a new class of tetracycline resistance genes which confers tetracycline resistance by ribosome protection. The complete DNA sequence of one such gene has been determined and is presented below. The invention also comprises proteins of the TetQ class, or active fragments thereof, that provide tetracycline resistance by ribosome protection.

Finally, the invention provides a promoter functional in *P. ruminicola* and an engineered *P. ruminicola* comprising expressible foreign DNA.

BRIEF DESCRIPTION OF THE DRAWINGS

FIG. 5A is an autoradiogram of a polyacrylamide SDS gel of in vitro transcription. translation products. Lane 1 contains products from the vector control, pFD160. Shown also are products from Tc$^s$ deletion derivatives pNFD13-2ΔRV (lane 2) and pNFD13-2Δ5 (lane 3), reduced Tc$^r$ deletion derivative pNFD13-2Δ4 (lane 4), Tc$^r$ deletion derivative pNFD13-2Δ3 (lane 5) and pNFD13-2Δ1 (lane 6), and intact pNFD13-2 (lane 7). The arrows in the right margin mark the two bands that were consistently unique to the SstI clone in maxicells. FIG. 5B shows an autoradiogram of soluble and membrane fractions from maxicells containing pNFD13-2: Lane 1, soluble fraction; Lane 2, membrane fraction.

FIGS. 6A and 6B show the deduced amino acid sequence of TetQ aligned with representatives of TetO (Campylobacter jejuni) and TetM (Streptococcus faecalis). The consensus of the sequenced ribosomal protection Tc$^r$ genes is displayed below these sequences. Upper case denotes conservation among the ribosome protection Tc$^r$ proteins. The four barred regions are regions of conservation in GTP-binding proteins [Halliday, J. Nucleotide Prot. Phosphoryl. Res., 9:435–448 (1984)]. Positions marked (*) were found to be involved directly in GTP binding and are invariant in all GTP-binding proteins [Jurnak, Science. 230:32–36 (1985)].

FIGS. 7A and 7B show the upstream sequence of tetQ. The endpoints of the pNFD13-2 deletions shown in FIG. 4 are indicated by numbers above the sequence. Only the last three characters of the deletion designations are given. The first letter in parenthesis at each deletion denotes Tc$^r$ expression in E. coli (R=resistant; I=intermediate; S=sensitive). The letter following the slash denotes Tc$^r$ expression in Bacteroides. The E. coli consensus −35 and −10 sequences are indicated by lines above the tetQ sequence. Below the tetQ upstream sequence is shown the upstream consensus of the tetM sequences from Staphylococcus aureus, Streptococcus faecalis, and Ureaplasma urealyticum and the tetO sequences from Campylobacter coli, Campylobacter jejuni, and Streptococcus mutans. Upper case letters denote bases that are conserved in all tetM and tetO sequences. Lower case letters denote bases that are not conserved in all cases, but are the consensus for that position. If data were not available for all six upstream sequences at a position, a lower case letter was used at that position.

DETAILED DESCRIPTION OF THE PRESENTLY PREFERRED EMBODIMENTS

Figure 1:
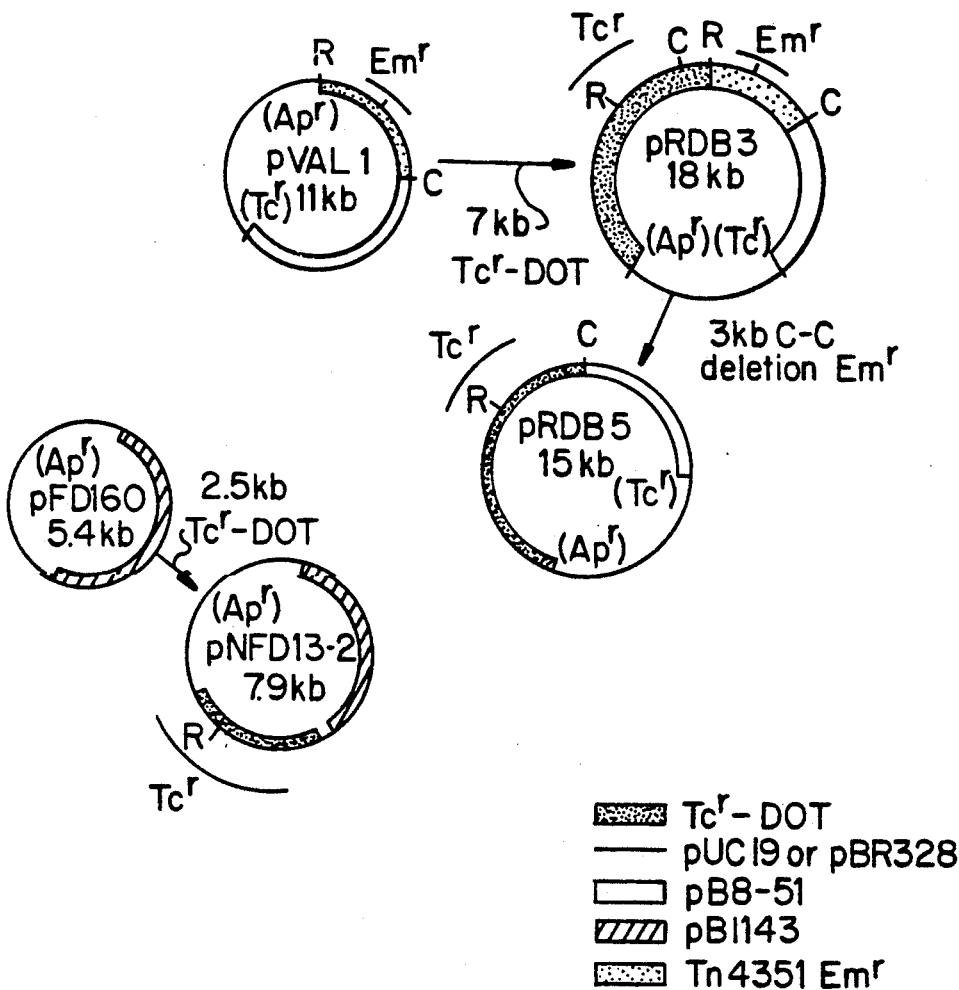
FIG. 1: A map of pVAL1 and a schematic diagram of the construction of pRDB3, pRDB5 and pNFD13-2. A partial map of the $Tc^rEm^r$ DOT element is indicated at the bottom of the figure, and the regions of this element which were cloned into the vectors are indicated by brackets under the map. Abbreviations for restriction sites are: R, EcoRI and C, ClaI. Only relevant restriction sites are shown: $Ap^r$=ampicillin resistance; $Tc^r$=tetracycline resistance; $Em^r$=erythromycin resistance.
Figure 1:
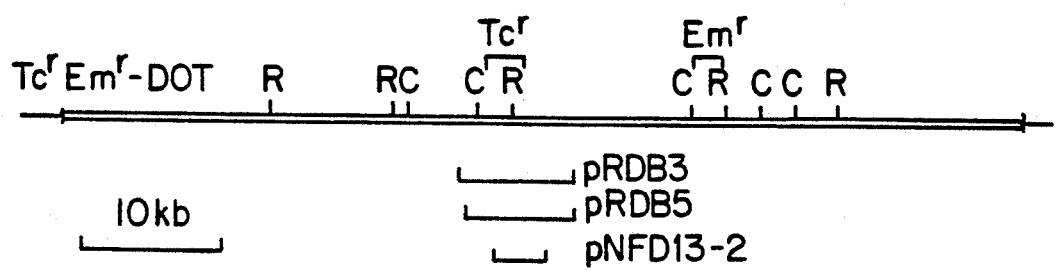

The method of the present invention involves conjugal transfer of shuttle vectors to Prevotella ruminicola. As explained in the Background section, Prevotella ruminicola are strains of bacteria previously classified as Bacteroides ruminicola. The criteria for determining whether a bacterium should be classified as B. ruminicola have been loose in the past. Examples of very authentic B. ruminicola (now P. ruminicola) strains having characteristics quite different than the colonic Bacteroides are B₁4, GA33, 23 and 118B. The degree of homology of 16S ribosomal RNA will probably be used as the standard to classify Bacteroides and Prevotella in the near future. Based on this standard, it is expected that B₁4, GA33, 23, 118B and bacteria whose 16S ribosomal RNA is at least 70% homologous with that of these strains will be classified as P. ruminicola.

The first step of the method of the invention is to transform an E. coli with a shuttle vector. Methods of transforming E. coli are well known in the art. Any strain of E. coli may be used, and numerous strains of E. coli are publicly available from such public depositories as the American Type Culture Collection (ATCC). The E. coli must have, or be engineered to have, a mobilization element which functions to transfer the shuttle vector from E. coli to a recipient colonic Bacteroides species. These elements may be introduced into E. coli using methods known in the art. Preferably, the mobilization element is an IncP plasmid, and most preferably the IncP plasmid R751. IncP plasmids such as R751 may be introduced into the E. coli by conjugation methods known in the art. Alternatively, E. coli strains, such as S17-1, are available which have the IncP plasmid inserted in their chromosomes.

Next, the E. coli is contacted with a species of colonic Bacteroides under conditions sufficient so that the shuttle vector is transferred from the E. coli to the colonic Bacteroides species. Methods of mating E. coli and colonic Bacteroides are known and include those described in Shoemaker, et al., J. Bacteriol., 166:959–965 (1986) and Thomson and Flint, FEMS Microbiol. Letters, 61: 101–104 (1989).

Any species of colonic Bacteroides may be used, and many species are available from public depositories, including the ATCC and the Virginia Polytechnic Institute (VPI) Anaerobe Collection (Blacksburg, Va.). The colonic Bacteroides species must contain, or be engineered to contain, a mobilization element which functions to transfer the shuttle vector from the colonic Bacteroides to P. ruminicola. These elements may be introduced into the colonic Bacteroides using methods known in the art such as conjugation. The mobilization element is preferably the conjugal element Tc$^r$Em$^r$ 12256. The Tc$^r$Em$^r$ 12256 element comprises approximately 120 kb of additional DNA not found in other Bacteroides conjugal elements. Although this segment of DNA has not been fully characterized, it is believed that it may enhance or increase efficiency of transfer. Most preferably, the colonic Bacteroides is Bacteroides uniformis containing the Tc$^r$Em$^r$ 12256 element.

The colonic Bacteroides species is then contacted with a strain of P. ruminicola under conditions sufficient so that the shuttle vector is transferred from the colonic Bacteroides species to the P. ruminicola. Many suitable species of P. ruminicola are available from public depositories, including the ATCC and the VPI Anaerobe Collection. A preferred P. ruminicola is B₁4.

Since P. ruminicola is extremely sensitive to oxygen, conjugation must take place under anaerobic conditions. Further, the use of a modified E (ME) medium has been found critical to obtaining transconjugants. The composition of ME medium is given in Example 1 below.

The present invention also comprises shuttle vectors suitable for transferring heterologous DNA into P. ruminicola. A shuttle vector is a vector which contains one or more replicons which allow it to replicate in more than one type of organism. In particular, the shuttle vectors of the present invention must be able to replicate in E. coli and colonic Bacteroides. They may also be able to replicate in P. ruminicola, or the shuttle vectors, or fragments thereof, may integrate into the P. ruminicola chromosome.

Suitable E. coli replicons are well-known and include the pUC and pBR series of plasmids. Replicons suitable for use in colonic Bacteroides include pB8-51, pBFTM10, and pBI143 [Salyers, et al., *CRC Critical Reviews in Microbiology*, 14:49–71 (1987): Odelson, et al., *Plasmid*, 17:87–109 (1987); Smith, *J. Bacteriol.*, 164:294–301 (1985)]. It has been found that the pB8-51 replicon also functions in P. ruminicola. Other P. ruminicola replicons can be identified using the teachings herein and, e.g., the TetQ gene of the invention which is known to be expressed in P. ruminicola.

The shuttle vectors of the invention must also be capable of being transferred from E. coli to a colonic Bacteroides species. Accordingly, they must contain a mobilization region which permits this transfer. The mobilization region must be one which is acted on by the mobilization element present in the E. coli to effect the transfer. Suitable mobilization regions are known. They include those on pBFTM10 (pDP1, pCG30), pB8-51 (pEG920, pVAL1), and pBI143 (pFD160) which are mobilized by IncP plasmids [Salyers, et al., *CRC Critical Reviews in Microbiology*, 14:49–71 (1987); Odelson, et al., *Plasmid*, 17:87–109 (1987); Shoemaker, et al., *J. Bacteriol.*, 166 959–965 (1986)].

The shuttle vectors must also be capable of being transferred from the colonic Bacteroides species to P. ruminicola, and they must contain a mobilization region which permits this transfer. The mobilization region must be one which is acted on by the mobilization element present in the colonic Bacteroides to effect the transfer. Suitable mobilization regions include the mobilization region of pB8-51 which is mobilized by Tc'Em' 12256. Other mobilization regions can be identified using the teachings herein.

The shuttle vector also comprises heterologous DNA sought to be transferred to P. ruminicola. "Heterologous DNA" is defined herein to mean DNA from a source other than the P. ruminicola strain which is to receive the heterologous DNA. The heterologous DNA may include DNA encoding enzymes involved in the fermentation of carbohydrates in the rumen, enzymes involved in the degradation of polysaccharides (such as xylanase or polysaccharases), other enzymes involved in rumen metabolism, and enzymes or groups of enzymes that synthesize substances that are beneficial to growth of cattle such as antibiotics. By transferring heterologous DNA to P. ruminicola, new and useful traits may be imparted to the recipient P. ruminicola. These traits can include those which will lead to more economical beef production.

The heterologous DNA is operatively linked to a promoter functional in P. ruminicola. A preferred promoter is a promoter of a TetQ gene (see discussion of TetQ genes below). Another preferred promoter is from the Tc'Em' DOT element. A particularly preferred promoter comprises the sequence (SEW ID NO: 1)

```
AAAAATCCTC CTACTTTTGT TAGATATATT TTTTTGTGTA ATTTTGTAAT   50
CGTTATGCGG CAGTAATAAT ATACATATTA ATACGAGTTA TTAATCCTGT  100
AGTTCTCATA TGCTACGAGG AGGTATTAAA AGGTGCGTTT CGACAATGCA  150
TCTATTGTAG TATATTATTG CTTAATCCAA,                      180
``` or active variants thereof. This promoter is the promoter region of the Tc' gene of the Tc'Em' element of B. thetaiotaomicron DOT and may be isolated from that gene or may be prepared by chemical synthesis. This promoter region is also strongly believed to be sufficient to initiate transcription in P. ruminicola. "Active variants" are promoters which have deletions, additions and/or substitutions of nucleotides as compared to the above sequence, but which are still able to initiate transcription in P. ruminicola.

The shuttle vector will also include one or more selection markers. Selection markers must be used to distinguish transformed E. coli from untransformed E. coli and to distinguish transconjugant colonic Bacteroides and P. ruminicola from non-transconjugants. It is also necessary to include selection markers that distinguish donor from recipient in mating mixtures. Many suitable selection markers are known and include antibiotic resistance, amino acid or other nutrient requirements, pH, and combinations of these. Preferred selection markers for P. ruminicola are TetQ tetracycline resistance genes. Especially preferred is the TetQ tetracycline resistance gene isolated from the Tc'Enm'-DOT element whose sequence is given below.

The various components of the shuttle vector may be isolated or synthesized and then assembled using techniques that are well known in the art. Indeed, one the most important aspects of the present invention is that it allows for the engineering of DNA that is to be introduced into P. ruminicola.

A preferred shuttle vector is pRDB5. The chimeric pRDB5 construct contains sequences from the plasmid pBR328, a cryptic colonic Bacteroides plasmid, pB8-51, and a colonic Bacteroides Tc' gene isolated from the Tc'Em'-DOT conjugal element. The restriction map of pRDB5 is shown in FIG. 1. Plasmid pRDB5 replicates in E. coli, colonic Bacteroides and P. rumininicola. Although it is not known whether pRDB5 replicates in, or transfers to, all colonic Bacteroides and P. ruminicola, this plasmid has a broad host range, and it is likely it can be used in many colonic Bacteroides and P. ruminicola.

In a preferred embodiment of the method of the present invention, E. coli were transformed with pRDB5. Then pRDB5 was mobilized from E. coli into B. uniformis by the IncP plasmid R751 which was present in the E. coli. Next, pRDB5 was conjugally transferred from B. uniformis to P. ruminicola B₁4 by the conjugal element Tc'Em' 12256 present in the B. uniformis. A combination of in vitro sections was utilized to identify P.

*ruminicola* B$_1$4 transconjugants. First, the *P. ruminicola* B$_1$4 recipient used was a rifampicin resistant mutant (rif$^r$) produced by growing *P. ruminicola* B$_1$4 on increasing levels of rifampicin to produce a spontaneous mutant. The rif$^r$ *P. ruminicola* B$_1$4 transconjugants could then be selected against donor *B. uniformis*, a species that is rifampicin sensitive. *B. uniformis* 1100 was chosen as a donor because it is a thymidine auxotroph, and the lack of thymidine in the selection medium could be used to select against that donor after matings with *P. ruminicola* B$_1$4. *B. uniformis* is also known to grow in medium containing vitamin K, whereas *P. ruminicola* B$_1$4 has no vitamin K requirement. Thus, vitamin K was also omitted from the selection medium. Finally, pH was used in the selection method because *P. ruminicola* B$_1$4 grows well at pH 6.2, whereas *B. uniformis* does not grow well at pH values lower than 6.8. The combination of selection for antibiotic resistance, lack of thymidine and vitamin K, and low pH provided a relatively clean background for selecting *P. ruminicola* B$_1$4 transconjugants. The transconjugants were distinguished from non-transconjugant *P. ruminicola* B$_1$4 because they were tetracycline resistant due to the expression of the foreign Tc$^r$ gene on pRDB5. The *P. ruminicola* B$_1$4 transconjugants were also tested for other traits that characterize *P. ruminicola* B$_1$4 and differentiate that strain from the donor *B. uniformis*. The results of the tests demonstrated that true *P. ruminicola* transconjugants containing pRDB5 were produced by the method of the invention.

The present invention also comprises transconjugant *P. ruminicola* prepared by the method of the invention and containing the shuttle vectors of the invention A particularly preferred transconjugant is *P. ruminicola* B$_1$4 containing pRDB5.

The invention further comprises a tetracycline resistance gene of the TetQ class, or fragments thereof that confer tetracycline resistance. The TetQ class is a new class of tetracycline resistance genes which confers tetracycline resistance by coding for proteins which protect ribosomes from the inhibitory binding of tetracyline.

The invention also comprises the proteins encoded by the TetQ genes (hereinafter "TetQ class of proteins"), or active fragments thereof. "Active fragments" of these proteins are fragments which are still capable of conferring tetracycline resistance. The DNA sequence of one TetQ gene (isolated from the Bacteroides conjugal element Tc$^r$Em$^r$-DOT) has been determined and is presented below in Example 2, along with the amino acid sequence of the protein encoded by the gene. The invention also comprises other DNA sequences which encode this same protein.

Hybridization studies using a portion of the sequenced gene indicates that TetQ genes are widespread in colonic Bacteroides. Given the stringency used in these experiments, it is estimated that the Tc$^r$ genes found in other Bacteroides Tc$^r$ strains share at least 80% identity with the sequenced gene. Also, the Tc$^r$ gene on the *P. ruminicola* plasmid pRRI4 appears to be a TetQ gene.

TetQ genes may be isolated from Bacteroides and Prevotella Tc$^r$ strains using known techniques. Alternatively, genes, or gene fragments, may be prepared using chemical synthesis.

Finally, the invention provides an engineered *P. ruminicola* containing expressible foreign DNA. "Foreign DNA" is used herein to mean DNA from a source other than *P. ruminicola*. Thus, "foreign DNA" is more narrow than "heterologous DNA," and heterologous DNA includes foreign DNA. "Engineered" is used to mean *P. ruminicola* not found in nature.

EXAMPLES

The restriction enzymes used in the following examples were obtained from Bethesda Research Laboratories, Gaithersburg, Md. They were used according to the manufacturer's instructions.

EXAMPLE 1

A. A Construction Of Shuttle Vectors

Four shuttle vectors were constructed. They were pRDB5, pVAL1, pRDB3, and pNFD13-2, shown in FIG. 1.

The vector pVAL1 carries the erythromycin resistance (Em$^r$) gene from the colonic Bacteroides transposon Tn4351 linked to portions of pBR328 (an *E. coli* replicon) and the cryptic Bacteroides plasmid pB8-51 (a colonic Bacteroides replicon). It was prepared as described in Valentine, et al., *J. Bacteriol.*, 170:1319–1324 (1988). Briefly, pBR328 (available from Boehringer Mannheim) was digested with EcoRI. The EcoRI fragment of Tn4351 [preparation from pBF4 described in Shoemaker, et al., *J. Bacteriol.*, 162:626.632 (1985)] was ligated to the EcoRI-digested pBR328 to produce pTB1. Plasmid pB8-51 was isolated from *Bacteroides eggerthi* by standard plasmid isolation techniques [See Maniatis, et al., *Molecular Cloning: A Laboratory Manual*, (Cold Spring Harbor, N.Y. 1982)]. It was then partially digested with TaqI. Next, ClaI digests of pTB1 were mixed with the TaqI digests of pB8-51 and ligated with T4 DNA ligase to produce pVAL1.

Vector pRDB3 was prepared by cloning a 7 kbp HincII fragment from a cosmid clone of the Tc$^r$Em$^r$-DOT element into pVAL1. The cosmid clone was prepared as described in Shoemaker, et al., *J. Bacteriol.*, 171:1294–1302 (1989). Then the cosmid clone was digested with HincII, and the resulting 7 kbp fragment containing the Tc$^r$ gene was ligated to PvuII digested pVAL1 to produce pRDB3.

Next, pRDB3 was digested with ClaI and religated to produce pRDB5. The result of this manipulation was to remove the Tn4351 Em$^r$ gene.

The vector pNFD13-2 comprises pFD160 having a 2.7 kbp fragment containing the Tc$^r$ gene from Tc$^r$Em$^r$-DOT cloned into the SstI site. Plasmid pFD160 was prepared as described in Smith, *J. Bacteriol.*, 164:294–301 (1985). It consists of HaeII-cleaved pBI143 (a colonic Bacteroides replicon) ligated to NdeI-digested pUC19 (an *E. coli* replicon). The 2.7 kbp fragment containing the Tc$^r$ gene was prepared as follows. Tn1000 insertions into pRDB3 were used to create convenient restriction sites. Transposon mutagenesis was performed by transforming an *E. coli* strain carrying the F plasmid on which Tn1000 resides with pRDB3. Tn1000 causes cointegrates to form between pRDB3 and the F plasmid. During conjugation, F::pRDB3 cointegrates are transferred to a recipient. In the recipient, the cointegrates resolve, leaving the F plasmid and pRDB3 with a Tn1000 insertion.

Restriction digests of the resulting pRDB3::Tn1000 isolates were screened by standard techniques (Maniatis, et al., supra), and the smallest clone that would express Tc$^r$ in colonic Bacteroides was identified. This clone was the 2.7 kbp fragment containing the Tc$^r$ gene and was excised with SstI.

B. Transformation Of *E. coli*

*E. coli* donor strains were constructed by introducing pRDB5, pVAL1, or pNFD13.2 into *E. coli* DH5αMCR [obtained from Bethesda Research Laboratory] or S17-1 [obtained from R. Simon, Universitat Bielefeld, Postfach 86–40, D-4800 Bielefeld 1, FRG; described in Simon, et al., Bio/Technology, 1:784.791 (1983)]. The plasmids were introduced into the *E. coli* strains by transformation techniques previously described [See Maniatis, et al., supra]. The IncP mobilizing plasmid R751 [See Meyer, et al., J. Bacteriol., 143:1362–1373 (1980)] was introduced into *E. coli* DH5αMCR by conjugation as described in Shoemaker, et al., *J. Bacteriol.*, 171:1294–1302 (1989); Thomson, et al., *FEMS Microbiol. Letters,* 61:101–104 (1989). *E. coli* S17-1 had a copy of the IncP plasmid RP4 already inserted in its chromosome. Both R751 and RP4 mobilize pRDB5, pVAL1, and pNFD13-2 from *E. coli* to *B. uniformis* at frequencies of $10^{-4}$ per recipient.

C. Preparation Of Colonic Bacteroides Donors

*B. uniformis* donor strains containing Tc$^r$Em$^r$ element 12256 and pRDB5 (Tc$^r$) or pNFD13-2 (Tc$^r$) were constructed by first introducing the plasmid pRDB5 or pNFD13-2 into *B. uniformis* 1100 [obtained from the VPI Anaerobe Laboratory, Blacksburg, Va.], as described previously [Shoemaker, et al., *J. Bacteriol.*, 166:959–965 (1986); Thomson, et al., *FEMS Microbiol. Letters,* 61:101–104 (1989)], and selecting for tetracycline resistance. Transconjugants carrying the Tc$^r$ plasmid were used as recipients in a mating with *B. uniformis* 1008 (Tc$^r$Em$^r$) obtained from the VPI Anaerobe Laboratory] to transfer the Tc$^r$Em$^r$ element 12256, with selection for Tc$^r$ and Em$^r$. The resulting strains were designated *B. uniformis* 1108 (pRDB5) and *B. uniformis* 1108 (pNFD13-2).

Similarly, to construct *B. uniformis* carrying the Tc$^r$Em$^r$ element 12256 and pVAL1 (Em$^r$), pVAL1 was first transferred from *E. coli* to *B. uniformis* 1100 by conjugation, with selection for Em$^r$. Then, the Tc$^r$Em$^r$ 12256 element was introduced by conjugation from *B. uniformis* 1008 to *B. uniformis* 1100 (pVAL1), with selection for Tc$^r$ and Em$^r$. The final strain was designated *B. uniformis* 1108 (pVAL1).

D. Mating with *P. ruminicola*

Next, the recipient, *P. ruminicola* B$_1$4 (obtained from Marvin Bryant, Dept. of Animal Sciences, University of Illinois, Urbana, Ill.), was mated with *E. coli* or *B. uniformis*. *E. coli* donor strains were grown in Luria broth (LB) to an O.D. (650 nm) of 0.15–0.20. *B. uniformis* 1108 strains were grown in TYG-Thy-K broth in 80% nitrogen-20% carbon dioxide to an O.D. (650 nm) of 0.15–0.20. Optical densities were measured in 18 mm diameter culture tubes in a Spectronic 20 spectrophotometer (Milton Roy Co., Rochester, N.Y.). TYG-Thy-K broth is trypticase-yeast extract-glucose broth [composition given in Holdeman, et al., *Anaerobe Laboratory Manual* (4th ed., Virginia Polytechnic Institute, Blacksburg, Va. 1977)] containing 100 μg/ml thymidine and 1 μg/ml vitamin K$_3$, with a final pH of 7.0–7.3.

*P. ruminicola* B$_1$4 was grown in MM10 broth at 80% nitrogen-20% carbon dioxide to an O.D. (650 nm) of 0.25–0.30. MM10 is similar to M10 medium previously described [*Anaerobe Laboratory Manual,* supra], except the concentration of trypticase and yeast extract was increased ten-fold and amylopectin was present as the carbohydrate source. Also, titanium citrate (0.15M) was added drop-wise until the resazurin became colorless (approximately 0.2–0.3 ml per liter of medium) prior to the addition of cysteine. The pH of this medium was 6.5–6.6. This medium, as were all media used for culturing *P. ruminicola,* was made in glass tubes sealed with a rubber stopper.

The *E. coli* or *B. uniformis* donor (30 ml) was centrifuged in a Sorvall GLC28 bench top centrifuge (SP/X rotor; Dupont Instruments, Wilmington, Del.) at 3,000 rpm for 15 minutes at room temperature to pellet the bacteria. The bacteria were then washed in 5 ml potassium phosphate buffer (0.1M, pH 7.0) and resuspended in 1 ml of TYG-Thy-K medium. Manipulations of *E. coli* or *B. uniformis* were performed under aerobic conditions.

*P. ruminicola* B$_1$4 (10 ml) was centrifuged in sealed culture tubes at 3,000 rpm for 15 minutes at room temperature as described above, and the supernatant fluid was removed with a sterile syringe.

The resuspended donor (*E. coli* or *B. uniformis*) (1 ml) and 5 ml of anaerobic 0.1M potassium phosphate buffer (pH 7.0) were injected into the tube. Anaerobic phosphate buffer was prepared by boiling phosphate buffer and cooling under a stream of oxygen-free carbon dioxide. After vortexing the tubes to dislodge the pelleted recipient, the bacterial mixture was centrifuged again in the sealed tubes, and the wash solution was withdrawn with a syringe. TYG-Thy-K medium (1.5 ml) and MM10 medium (1.5 ml) were injected into the tube, and the tube was vortexed to resuspend the bacteria. The resuspended mixture was injected into a sealed anaerobic tube containing a slant of modified E agar medium ("ME"), pH 6.8, for the mating. ME is the same as Sweet E medium previously described (*Anaerobe Laboratory Manual,* supra), except it contains glucose, as the only carbohydrate, and 100 ug/ml thymidine. Agar was added to a final concentration of 2%. The tubes were then centrifuged as described above to pellet the bacteria on the slants. The tubes were inverted gently, and the supernatant fluid removed with a syringe. The tubes were then incubated upside down at 37° C. for 15–18 hours.

After incubation, 1 ml of MM10 (pH 6.6), containing no thymidine or vitamin K was added to the slant tubes, and the tubes were vortexed. Next, resuspended bacteria were removed with a sterile syringe which had been gassed out with nitrogen-carbon dioxide.

To select for transconjugants, 0.1–0.2 ml of resuspended cells, or 0.1–0.2 ml of a 1:10 dilution, were inoculated into a roll tube containing MM10-Rif-Tc or MM10-Rif-Em selection medium. MM10-Rif (pH 6.2) medium consisted of MM10 containing 2% agar and 40 ug/ml rifampicin. For selection of transconjugants, either tetracycline (final concentration of 5 ug/ml) or erythromycin (final concentration of 5 ug/ml) was added to the MM10-Rif medium to produce MM10-Rif-Tc and MM10-Rif-Em, respectively.

To enumerate the total number of *B. uniformis* donors, 0.1 ml of a $10^{-6}$ dilution of the resuspended cells was plated on TYG-Thy-K agar plates and incubated in a GasPak jar. To enumerate the *E. coli* donors, 0.1 ml of a $10^{-6}$ dilution was plated on LB agar and incubated aerobically. To enumerate the *P. ruminicola* B$_1$4 recipients, 0.1 ml of a $10^{-6}$ and a $10^{-8}$ dilution were inoculated into an MM10-Rif roll tube. All incubations were done at 37° C. for 3.4 days.

E. Results Of E. coli-P. ruminicola Matings

When the transfer of plasmids pVAL1, pNFD13-2, and pRDB5 from *E. coli* to *P. ruminicola* was attempted, no Tc$^r$ or Em$^r$ *P. ruminicola* transconjugants were detected. As a result, *B. uniformis* was used as an intermediate donor for *P. ruminicola* as described in the next section.

F. Results Of B. uniformis-E. coli Matings

*B. uniformis* 1108 (pRDB5), *B. uniformis* 1108 (pVAL1), or *B. uniformis* 1108 (pNFD13-2), prepared as described above, were mated with *E. coli* HB101 or EM24 to determine whether the *B. uniformis* recipients carrying a conjugal Tc$^r$Em$^r$ 12256 element and a plasmid were capable of mobilizing the plasmid at high frequency. The procedure for the *B. uniformis-E. coli* mating has been described previously [See Shoemaker, et al., *J. Bacteriol.*, 166:959-965 (1986); Thomson, et al., *FEMS Microbiol. Letters*, 61:101-104 (1989)]. Mobilization of these plasmids from *B. uniformis* to *E. coli* occurred at frequencies of $10^{-4}$–$10^{-5}$ per recipient (see Table 1 below).

G. Results Of B. uniformis-P. ruminicola Matings

To test for transfer of the plasmids from *B. uniformis* to *P. ruminicola* B$_1$4, a selective medium allowing growth of *P. ruminicola* but not *B. uniformis* had to be developed. Being able to detect transfer frequencies as low as $10^{-9}$ per recipient was the criterion.

First, the antibiotic sensitivity of *P. ruminicola* B$_1$4 was tested. Minimal inhibitory concentrations for various antibiotics were determined by inoculating MM10 containing different concentrations of antibiotic and incubating for 48 hours. Antibiotic concentrations tested were 5, 10, 20, 50, 100 and 200 ug/ml. In the case of tetracycline and erythromycin, resistance levels on MM10 agar medium were also determined.

*P. ruminicola* B$_1$4 was found susceptible to rifampicin (10 ug/ml), tetracycline (2 ug/ml), erythromycin (1 ug/ml), gentamicin (20 ug/ml), and ampicillin (5 ug/ml). It was resistant to chloramphenicol (10 ug/ml), kanamycin (50 ug/ml), trimethoprim (200 ug/ml), and nalidixic acid (100 ug/ml).

*P. ruminicola* B$_1$4 was susceptible to all of the antibiotics which inhibited growth of *B. uniformis* except chloramphenicol. Accordingly, chloramphenicol was first used to select for *P. ruminicola* B$_1$4 and against the donor. Mixtures of *B. uniformis* and *P. ruminicola* B$_1$4 were plated on MM10 agar containing 10 ug/ml chloramphenicol. Donor *B. uniformis* colonies were still able to grow enough to obscure true transconjugants. Therefore, another resistance for selecting *P. ruminicola* recipients was required.

A spontaneous rifampicin resistant (Rif$^r$) mutant of *P. ruminicola* B$_1$4 was isolated by inoculating the bacteria into MM10 broth medium containing progressively higher concentrations of rifampicin. By growing *P. ruminicola* B14 on successively higher concentrations, a spontaneous mutant of *P. ruminicola* B$_1$4 was obtained which would grow in rifampicin concentrations as high as 60 ug/ml. The spontaneous Rif$^r$ mutant was determined to be a derivative of *P. ruminicola* B$_1$4 by comparing its NotI digest pattern with that of the original B$_1$4 strain. The restriction enzyme digest patterns were identical. This Rif$^r$ strain was used in matings to provide a selection for the *P. ruminicola*. This method of producing the rifampioin mutant is a well known method of producing suitable *P. ruminicola* rifampicin resistant mutants can be produced in this manner.

However, using the Rif$^r$ derivative, *P. ruminicola* B$_1$4R, as a recipient and selecting for rifampicin resistance did not allow for the detection of transfer frequencies as low as $10^{-9}$ per recipient because spontaneous Rif$^r$ mutants of *B. uniformis* 1108 occurred at a frequency of $10^{-7}$.

Accordingly, a combination of selections had to be used. First, the *P. ruminicola* B$_1$4 rifampicin resistant mutant was used. *B. uniformis* 1100 was chosen as a donor because it is a thymidine auxotroph, and the lack of thymidine in the selection medium could be used to select against that donor after matings with *P. ruminicola* B$_1$4. However, spontaneous reversion to wild type occurs at relatively high frequencies ($10^{-6}$). *B. uniformis* is also known to grow in medium containing vitamin K, whereas *P. ruminicola* B$_1$4 has no vitamin K requirement. Thus, vitamin K was also omitted from the selection medium. Finally, pH was used in the selection method because *P. ruminicola* B$_1$4 grows well at pH 6.2, whereas *B. uniformis* does not grow well at pH values lower than 6.8. The combination of selection for antibiotic resistance, lack of thymidine and vitamin K, and low pH provided a relatively clean background for selecting *P. ruminicola* B$_1$4 transconjugants.

Using this selection medium and using a donor to recipient ratio of 1.5-3.0:1.0, Tc$^r$ transconjugants were detected in a mating between *B. uniformis* 1108 (pRDB5) and *P. ruminicola* B$_1$4 (Rif$^r$) at frequencies of $10^{-6}$–$10^{-7}$ per recipient (see Table 1). No transconjugants were detected in matings in which the donor was *B. uniformis* 1108 (pNFD13-2) or *B. uniformis* 1108 (pVAL1).

The ability of the transconjugants to grow in various media was tested to rule out the possibility that the apparent transconjugants were spontaneous Rif$^r$ or Rif$^r$Thy$^+$ mutants of the *B. uniformis* donor. Growth on TYG, no growth on TYG-Thy, no growth in MM10 containing gentamicin, and growth in MM10 containing xylan instead of glucose was observed. These phenotypic characteristics indicated that the transconjugants were of *P. ruminicola* origin rather than *B. uniformis*.

DNA analysis of *P. ruminicola* B$_1$4 transconjugants was performed. Plasmids were isolated from *P. ruminicola* B$_1$4 transconjugants by the Ish-Horowitz modification of the Birnbom and Doly procedure as described in Maniatis, et al., *Molecular Cloning: A Laboratory Manual* (Cold Spring Harbor Laboratory, Cold Spring Harbor, N.Y. 1982). Southern blots were also performed as described in Maniatis, et al., supra. Total DNA was prepared by standard methods as described in Saito, et al., *Biochem. Biophys. Acta.* 72:619-629 (1963); Shoemaker, et al., *J. Bacteriol.*, 171:1294-1302 (1989); Shoemaker, et al., *J. Bacteriol.*, 166:959-965 (1986).

Plasmid preparations made from *P. ruminicola* B$_1$4R had a background staining material that made it difficult to see plasmid DNA unambigiously. However, when a plasmid preparation was used to transform *E. coli* and pRDB5 was recovered in *E. coli*, the restriction profile of this plasmid was identical to that of the original pRDB5.

Figure 2A:
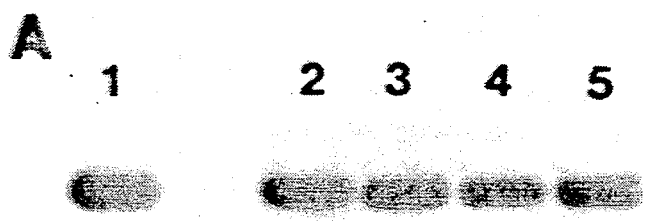
FIG. 2A: Total DNA from the *B. uniformis* 1108 donor containing pRDB5 (lane 1), and four *P. ruminicola* $B_14Tc^r$ transconjugants (lanes 2-5) was digested with EcoRI. The Southern blot was probed with pFD160 which cross-hydridizes with pRDB5 but not with *P. ruminicola* $B_14$ DNA.

Additionally, total DNA (plasmid plus chromosome) was isolated from apparent *P. ruminicola* transconjugants, digested with EcoRI and subjected to Southern blot analysis. EcoRI cuts once in pRDB5 to produce a 15 kb linear segment. The DNA digests were separated on a 1.0% agarose gel and blotted onto Optibind (Schleicher and Schuell). The digests were then probed with $^{32}$P-labelled pFD160. The pFD160 plasmid hybridizes with the pBR328 sequences in pRDB5, but not with the Tc$^r$ gene. All of the putative transconjugants contained a single band of the correct size which hybridized with the probe (see FIG. 2A).

Figure 2B:
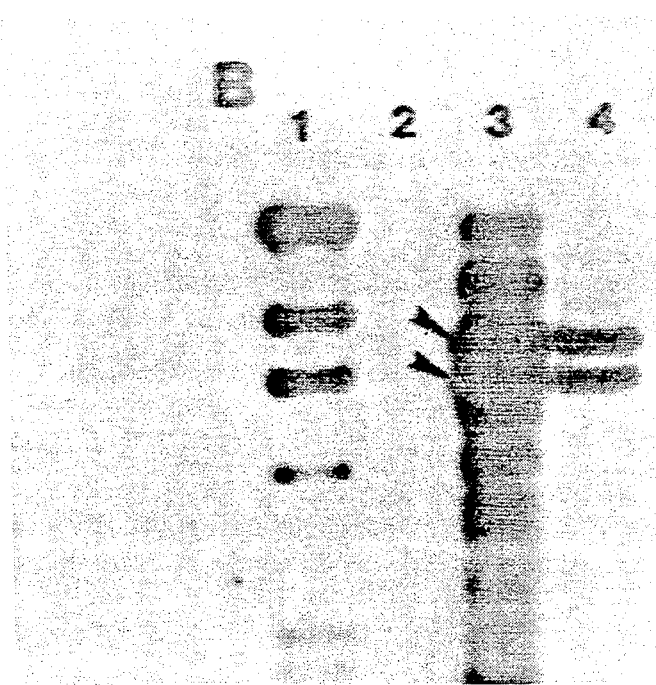
FIG. 2B: Total DNA from the *P. ruminicola* $B_14R$ recipient (lane 2), the *B. uniformis* 1108 donor (lane 3) and one of the *P. ruminicola* $B_14$ transconjugants (lane 4) was digested with EcoRI and HindIII. The Southern blot was probed with XBU4422::pEG920. This probe hybridizes not only with pBR328 sequences on pRBD5 but also with the $Tc^rEm^r$ 12256 element in the donor. The two bands corresponding to pRDB5 are indicated in lane 3 by arrows. Lane 1 contains DNA size standards. The largest four standards are 23.1 kb, 9.4 kb, 6.7 kb and 4.4 kb, respectively.

Total DNA from *B. uniformis*, *P. ruminicola* B$_1$4, and *P. ruminicola* transconjugants were also digested with HindIII and EcoRI restriction enzymes, and the digests blotted onto Optibind. The blot was hybridized with labelled XBU4422::pEG920 [prepared as described in Shoemaker, et al., *J. Bacteriol.*, 172:1694–1702 (1990)], a probe which detects pRDB5 and the TcEm$^r$ 12256 element. If the apparent transconjugants were Thy$^+$-Rif$^r$ mutants of *B. uniformis* 1108 (pRDB5), the Southern blot would show a number of bands, including the two bands produced from a HindIII-EcoRI digest of pRDB5. As can be seen from FIG. 2B, a mixture of bands due to pRDB5 and the Tc$^r$Em$^r$ 12256 element was seen in the *B. uniformis* donor, whereas only the bands associated with pRDB5 were seen in the transconjugant. These results indicated that the transconjugants were not revertants of the *B. uniformis* donor.

Figure 3:
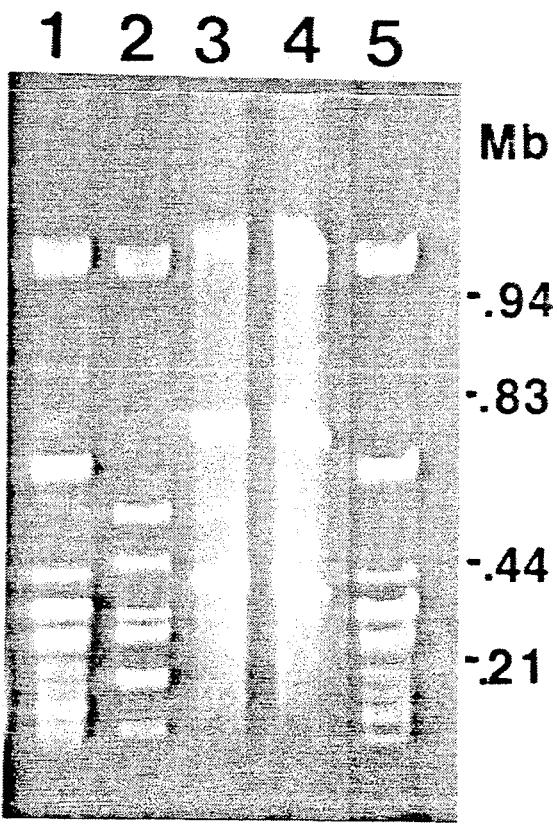
FIG. 3: Results of pulse field electrophoresis to verify the identity of P. ruminicola B₁4 Tc$^r$ transconjugants. NotI digests of DNA from the donor, B. uniformis 1108 carrying pRDB5, are shown in lanes 1 and 5. NotI digested DNA from P. ruminicola GA33 (lane 2), B₁4R (lane 3) and one of the B₁4 pRDB5 transconjugants (lane 4) are also shown. The NotI pattern of P. ruminicola B₁4 is identical to that of B₁4R (data not shown). The migration distances of some of the yeast chromosomes size standards are shown in megabases (Mb) at the side of the gel.

The NotI restriction enzyme digest patterns of DNA from *B. uniformis*, *P. ruminicola* B$_1$4R, and a *P. ruminicola* B$_1$4 transconjugant were compared on pulsed field gels to determine whether a Tc$^r$ contaminant having properties similar to *P. ruminicola* had been isolated instead of true transconjugants. The NotI digest pattern of *P. ruminicola* B$_1$4 differs not only from that of *B. uniformis* 1108, but also differs from that of other *P. ruminicola* strains (data not shown). As shown in FIG. 3, the NotI restriction patterns of the *P. ruminicola* B$_1$4R recipient and the Tc$^r$ transconjugant were identical to each other and to that of *P. ruminicola* B$_1$4.

The combined data show that true *P. ruminicola* transconjugants were obtained.

No transfer of pNFD13-2 to *P. ruminicola* B$_1$4 was detected. Since pNFD13-2 has the same Tc$^r$ gene as pRDB5 but derives its replication region from a different plasmid, the lack of transconjugants was most likely due to failure of the pNFD13-2 replication origin (pBI143) to work in *P. ruminicola* B$_1$4. However, there is a 4 kbp region upstream of the Tc$^r$ gene which is present in pRDB5 but not in pNFD13-2. This region seems to have no effect expression of the Tc$^r$ gene in *B. uniformis*, but it might affect expression in *P. ruminicola* B$_1$4. Since pNFD13-2 was mobilized from *B. uniformis* to *E. coli* at frequencies comparable to mobilization frequencies seen with pRDB5, it is possible that pNFD13-2 is getting into *P. ruminicola* B$_1$4 but is lost because it cannot replicate. If so, pNFD13-2 could serve as a suicide vector for introducing DNA into the chromosome of *P. ruminicola* B$_1$4.

Genetic manipulation of *P. ruminicola* would be easier if *E. coli* were the donor. Failure to demonstrate transfer of pRDB5 from *E. coli* to *P. ruminicola* could be due to the failure of IncP plasmids to mediate formation of mating pairs between *E. coli* and *P. ruminicola*. However, since IncP plasmids mediate mating between *E. coli* and the colonic Bacteroides strains, this seems unlikely. A more likely possibility is that the transfer frequency is lowered by the anaerobic mating conditions. Aerobic matings with the oxygen-sensitive *P. ruminicola* are not feasible. Nonetheless, it may be possible to find conditions that raise the frequency of mating and allow *P. ruminicola* to survive. Finally, restriction enzymes in *P. ruminicola* may prevent survival of pRDB5 introduced from *E. coli*.

TABLE 1

Transfer frequencies of various shuttle vectors from *B. uniformis* to either *B. ruminocola* B$_1$4 or *E. coli*.

| Donor strain | Frequency of transfer from *B. uniformis* to | |
|---|---|---|
| | *E. coli* | *B. ruminicola* |
| *B. uniformis* 1108 (pRDB5) | $3 \times 10^{-4a}$ | $10^{-7} - 10^{-6}$ |
| *B. uniformis* 1108 (pNFD13-2) | $1 \times 10^{-4}$ | $<10^{-9}$ |
| *B. uniformis* 1108 (pVAL1) | $1 \times 10^{-4}$ | $<10^{-9}$ |
| *B. uniformis* 1104 (pRBD3) | $1 \times 10^{-5}$ | $<10^{-9}$ |
| *B. uniformis* 1108 (pRDB5-2)$^b$ | $2 \times 10^{-4}$ | $10^{-7} - 10^{-6}$ |

$^a$Frequencies are given as transconjugants per recipient. Numbers represent the mean of at least three separate experiments.
$^b$pRDB5-2 is pRDB5 isolated from a *B. ruminicola* B$_1$4 transconjugant in the *B. uniformis* 1108 background.

EXAMPLE 2

The Bacteroides Tc$^r$ gene, originally derived from the Bacteroides conjugal element Tc$^r$Em$^r$-DOT [Shoemaker, et al., *J. Bacteriol.*, 171:1294–1302 (1989)], was subcloned on a 2.7 kbp fragment, and the 2.7 kbp fragment was sequenced. The complete sequence of the fragment is shown below in Chart A. Computer analysis of the DNA sequence, translation into amino acid sequence, and comparisons to amino acid sequences of other tetracycline resistance peptides were performed. The amino acid sequence of the gene product is presented below in Chart B. A promoter region functional n Bacteroides species was identified. Its sequence is shown below in Chart C. This promoter region is also strongly believed to be sufficient to initiate transcription in *P. ruminicola*.

The gene coded for a protein of the ribosome protection type of tetracycline resistance. However, the amino acid sequence coded for by the cloned gene was found to be only about 40% identical to sequences coded for by the TetM and TetO genes, two known classes of ribosome protection type tetracycline resistant genes. Accordingly, it was concluded that the Bacteroides Tc$^r$ was clearly in a separate DNA-DNA hybridization class from TetM and TetO and constituted its own DNA hybridization class. This new class of tetracycline resistance genes is designated TetQ. The experiments and analyses performed, and the Bacteroides Tc$^r$ gene and its gene product, will now be described in detail.

A. Materials and Methods

1. Strains and Growth Conditions

Strains used in this study are listed in Table 2. *E. coli* DH5α was obtained from Bethesda Research Laboratory. *B. thetaiotaomicron* strains BT 4001, BT4002, BT4004, BT4007 and BT4008 and *B. uniformis* BU10001 are described in Shoemaker and Salyers, *J. Bacteriol.*, 170:1651–1657 (1988). *B. thetaiotaomicron* strains 5482 and 2808, *B. uniformis* strains C7-17, 2537, T1-1, *B. distasonas* strains 4243, C30-45, 6308, and *B. caccae* strains 3452A and 8608 are described in Johnson, *J. Syst. Bacteriol.*, 28:245–256 (1978). *B. fragilis* AK87 was obtained from A. Kuritza, Yale University Medical School, New Haven, CT. *E. coli* LCD44 was obtained from Dr. John Cronon, Jr., University of Illinois, Urbana, Ill.

Bacteroides strains were grown either in prereduced Trypticase (BBL Microbiology Systems)-yeast extract-glucose (TYG) [Holdeman, et al., *Anaerobe Laboratory Manual*, supra] under an 80% $N_2$/20% $CO_2$ atmosphere or on TYG agar plates in a GasPak jar. *E. coli* strains were grown in Luria broth (LB) or on LB agar plates unless otherwise indicated.

2. Plasmids

The preparation of pNFD13-2 is described above in Example 1. As discussed there, it contains a 2.7 kbp insert containing the $Tc^r$ gene of the $Tc^rEm^r$-DOT element. Plasmid pNFD13-6 is identical to pNFD13-2, but with the 2.7 kbp insert in the opposite orientation.

3. DNA Isolation and Analysis

Plasmids were isolated from *E. coli* by the Ish-Horowitz modification of the Birnboim and Doly method [Maniatis, et al., supra]. Chromosomal DNA from Bacteroides was isolated by the method of Saito and Miura, *Biochim. Biophys. Acta.* 72:619–629 (1963). Restriction digestion and ligation with T4 DNA ligase followed standard procedures (Maniatis, et al., supra). Electrophoretic resolution of restriction digests was done in 0.8–1.0% agarose slab gels in 1X or 4X GGB (1X: 0.04M Tris, 0.02M sodium acetate, 0.002M EDTA). Gels were stained with ethidium bromide (1 µg/ml) and photographed. Plasmids were introduced into *E. coli* employing the transformation procedure of Lederberg and Cohen, *J. Bacteriol.* 119:1072–1074 (1974).

4. Southern Hybridization

For Southern blot hybridization analysis, DNA was digested with restriction enzymes and electrophoresed on a 1% agarose gel. The DNA was transferred to Millipore HAHY nitrocellulose paper by capillary blotting (Maniatis, et al., supra). Nick translation was used to label DNA probes with [$\alpha$-$^{32}$P]-dCTP [Rigby, et al., *J. Mol. Biol.*, 113:237–251 (1977)]. Probes were hybridized to DNA on the nitrocellulose paper for 24 hours at 42° C. in a hybridization solution containing 50% formamide (Maniatis, et al., supra). Following hybridization, blots were washed twice for 30 minutes each with 2X SSC (0.3M NaCl and 0.03M sodium citrate) containing 0.2% sodium dodecyl sulfate (SDS), then twice with 0.2% SDS in 0.5X SSC at 60° C. Blots were then analyzed using autoradiography.

5. Minimum Inhibitory Concentration (MIC) of Tetracycline

To test for expression of the 2.7 kbp clone of the $Tc^r$ gene and its various deletion derivatives in *E. coli* and *B. thetaiotaomicron*, MIC values were determined. When *E. coli* was the host, ampicillin (100 µg/ml) or tetracycline (3 µg/ml) was added to inoculum cultures to maintain plasmids in plasmid-bearing strains. In most experiments, MIC values were determined using the tube dilution method. Cells (0.1 ml) from overnight inoculum cultures were introduced into LB broth medium containing serially incremented concentrations of tetracycline. Increments of 5 µg/ml were used. Tubes were incubated at 37° C. and scored visually for growth at 12 and 24 hours. In some experiments, the level of resistance was determined by patching cultures onto LB agar plates containing different concentrations of antibiotic and scoring growth after 24 hours.

To test for expression in Bacteroides, vectors containing various subclones of the 2.7 kbp clone of the $Tc^r$ gene were mobilized into *B. thetaiotaomicron* as described previously [Shoemaker, et al., *J. Bacteriol.*, 171:1294–1302 (1989); Shoemaker, et al., *J. Bacteriol.*, 162:626–632 (1985)], with selection for $Tc^r$. Transfer frequencies were several logs above background. Thus, failure to obtain a $Tc^r$ transconjugant was a reasonable indication that the deletion clone failed to express $Tc^r$ in Bacteroides. In Bacteroides, MIC determinations were done in TYG broth medium with serially incremented concentrations of tetracycline.

6. Maxicells

The maxicell procedure was executed as described by Sancar, et al., *J. Bacteriol.*, 137:692–693 (1979), with *E. coli* LCD44 as host. Samples were solubilized by incubation in SDS or lithium dodecyl sulfate solubilizing solution at 37° C. to avoid possible aggregation. Proteins from maxicells were separated by electrophoresis on 11% highly cross-linked SDS polyacrylamide gels as described by Hashimoto, et al., *Anal. Biochem.*, 112:192–199 (1983). Following electrophoresis, gels were stained with Fast Stain (Zoion Research Inc., Allston, Mass.), dried onto filter paper under vacuum, and autoradiographed. Molecular weight markers from BRL, Gaithersburg, Md., were used for size estimation. Maxicell fractionation was performed using an adaptation of the method of Tai and Kaplan, *J. Bacteriol.*, 164:83–88 (1985).

7. In Vitro Transcription and Translation

Proteins encoded by plasmid templates were compared using an *E. coli*-derived in vitro transcription-translation system [DeVries and Zubay, *Proc. Nat. Acad. Sci. USA.* 57:1010–1012 (1967)] in kit form (Amersham, Arlington Heights, Ill.). Radiolabeled proteins were resolved on 11% highly cross-linked SDS polyacrylamide and detected by autoradiography as described above.

8. DNA Sequencing and Analysis

Figure 4:
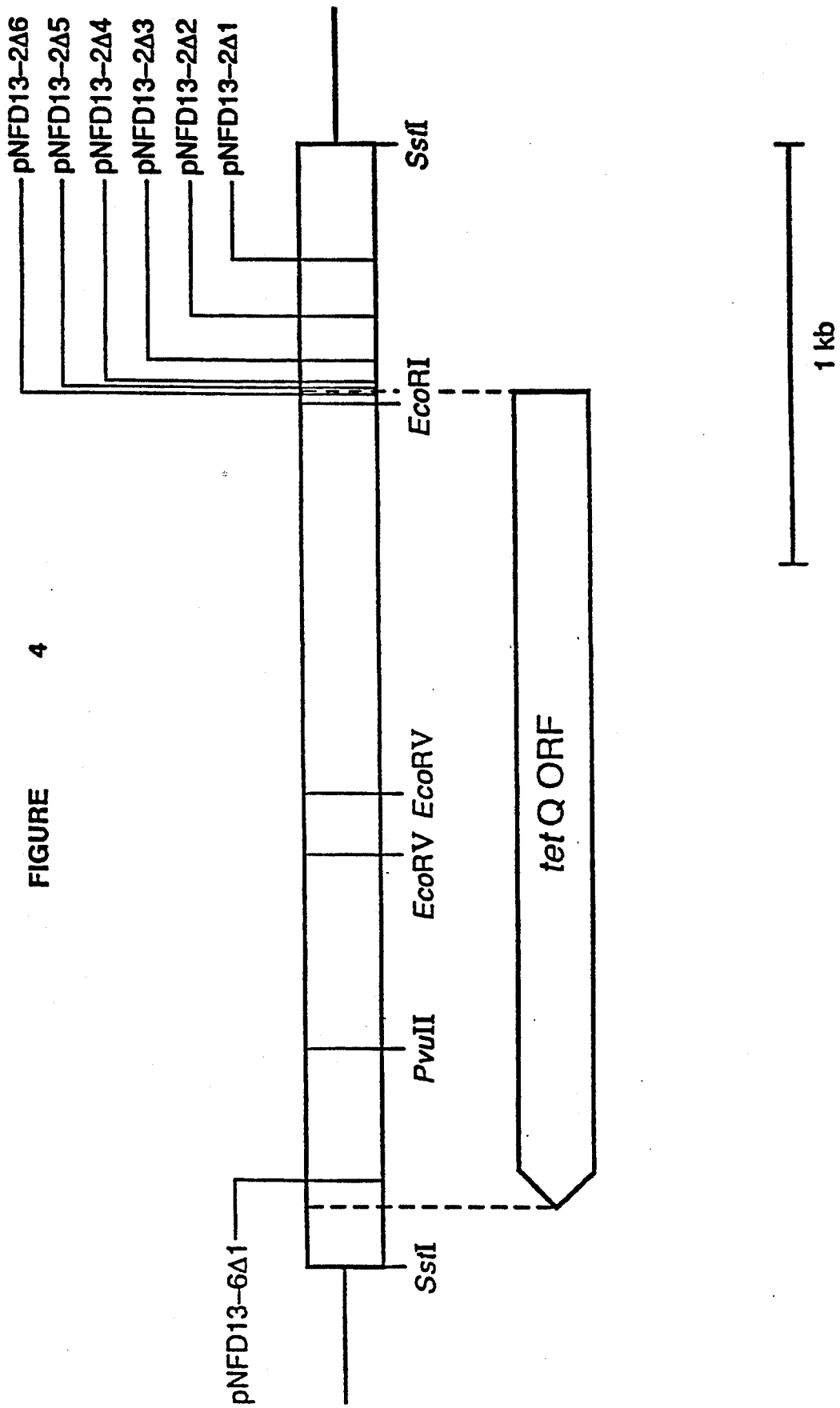
FIG. 4 is a partial restriction map of the 2.7 kbp SstI clone of the Tc$^r$ gene from B. thetaiotaomicron DOT. Important deletion derivatives are indicated by the labeled brackets. The orientation and extent of the large open reading frame encoding TetQ are indicated below by the arrow.

The region sequenced in this study was the 2.7 kbp SstI fragment from pNFD13.2 and pNFD13-6. Progressive unidirectional deletions were introduced into the insert DNA using an adaptation of the exonuclease III procedure of Henikoff, *Gene*, 28:351 (1984), provided in kit form (Erase-a-Base System by Promega, Madison, Wisc.). (See FIG. 4) Both strands were sequenced by the dideoxy chain termination reaction with the T7 DNA polymerase variant and reagents provided in the Sequenase 2.0 kit Biochemicals, Cleveland, Ohio). Computer analysis of DNA sequence, translation into amino acid sequence and comparisons to amino acid sequences of other tetracycline resistance peptides were performed using Genetics Computer Group (GCG) software (Devereux, et al., *Nucl. Acids Res.*, 12:387–395 (1985)) on a MicroVAX computer system. The sequences of tetracycline resistance and elongation factor genes used in this study were obtained from GenBank and are listed with accession numbers in Table 3.

B. Results

1. Expression of the Bacteroides Tetracycline Resistance Gene in *E. coli*

The $Tc^r$ gene from *B. thetaiotaomicron* DOT was localized to a 2.7 kbp SstI fragment in the constructs pNFD13-2 and pNFD13-6, which contained the insert in opposite orientations. Though these plasmids were originally constructed to test for expression in Bacteroides, we examined them for expression in *E. coli* because it was possible that the lac promoter adjacent to the cloned SstI fragment would drive Tc$^r$ expression in *E. coli*. Because *E. coli* carrying low copy number cosmid clones of the Tc$^r$ gene did not grow on LB plates containing 5 or 10 μg/ml tetracycline, Shoemaker, et al. had reported that the *Bacteroides* Tc$^r$ gene did not function in *E. coli* [Shoemaker, et al., *J. Bacteriol.*, 171:1294-1302 (1989)]. However, it was found that the 2.7 kbp SstI insert in the higher copy number pUC19-based vector, pFD160R, allowed *E. coli* to grow on LB agar plates containing 5 μg/ml tetracycline.

Following pregrowth in LB containing 100 μg/ml ampicillin, *E. coli* DH5α carrying the SstI clone had a tetracycline MIC value of 40 μg/ml for pNFD13-2 and a value of 25 μg/ml for pNFD13-6. However, when the inoculum culture was grown in LB containing sub-inhibitory tetracycline (1 μg/ml), differences in MIC between the clones diminished; the MIC values for pNFD13-2 and pNFD13-6 were 50 μg/ml and 40 μg/ml, respectively. The fact that the MIC values of both orientations were comparable indicated that the promoter being recognized was on the cloned fragment, and therefore was not the lac promoter. Moreover, addition of IPTG to the growth medium had no effect upon MIC levels. Interestingly, MIC values obtained on LB agar plates for *E. coli* bearing pNFD13-2 and pNFD13-6 were significantly lower than the values obtained in broth medium (plate MIC of 10 μg/ml for pNFD13-2).

2. Localization of the Bacteroides Tc$^r$ Gene

Initially, two deletions in the 2.7 kbp SstI segment were created by digesting pNFD13-2 with EcoRV and religating to form pNFD13-2ΔRV and by digesting pNFD13-6 with EcoRI and religating to form pNFD13-6ΔRI. The MIC of DH5α bearing pNFD13-2ΔRV or pNFD13-6ΔRI was the same as that for DH5α without plasmid (2 μg/ml). Loss of resistance in both deletions indicated that the Tc$^r$ gene spanned the internal 0.9 kbp EcoRI-EcoRV region of the SstI clone. Further localization of the gene was undertaken using exonuclease III to create progressive unidirectional deletions in the 2.7 kbp SstI insert from the pFD160 polylinker. (See FIG. 4) Deletion pNFD13-2Δ3, which extended from the right to within 100 bp of the EcoRI site, did not affect resistance in *E. coli*. Deletion pNFD13-2Δ4, which extended to within 50 bp of the EcoRI site, decreased the MIC without completely eliminating resistance. Deletions into or through the EcoRI site abolished Tc$^r$ in *E. coli*. Deletion pNFD13-6Δ1, which extended 200 bp into the other end of the SstI fragment, also abolished Tc$^r$. Thus, it appeared that the genetic information essential for Tc$^r$ expression in *E. coli* spanned a 2.1 kbp region in the SstI insert DNA.

A larger region was required for Tc$^r$ expression in Bacteroides than in *E. coli*. Deletion construct pNFD13-2Δ3, which conferred full resistance on *E. coli*, did not confer resistance on Bacteroides. The largest of the exonuclease III deletions from the right which retained full Tc$^r$ activity in Bacteroides was pNFD13-2Δ2. Thus, it appeared that an additional region of approximately 200 bp was required for expression in Bacteroides.

3. Size and Cellular Location of the Tc$^r$ Gene Product

Figure 5A:
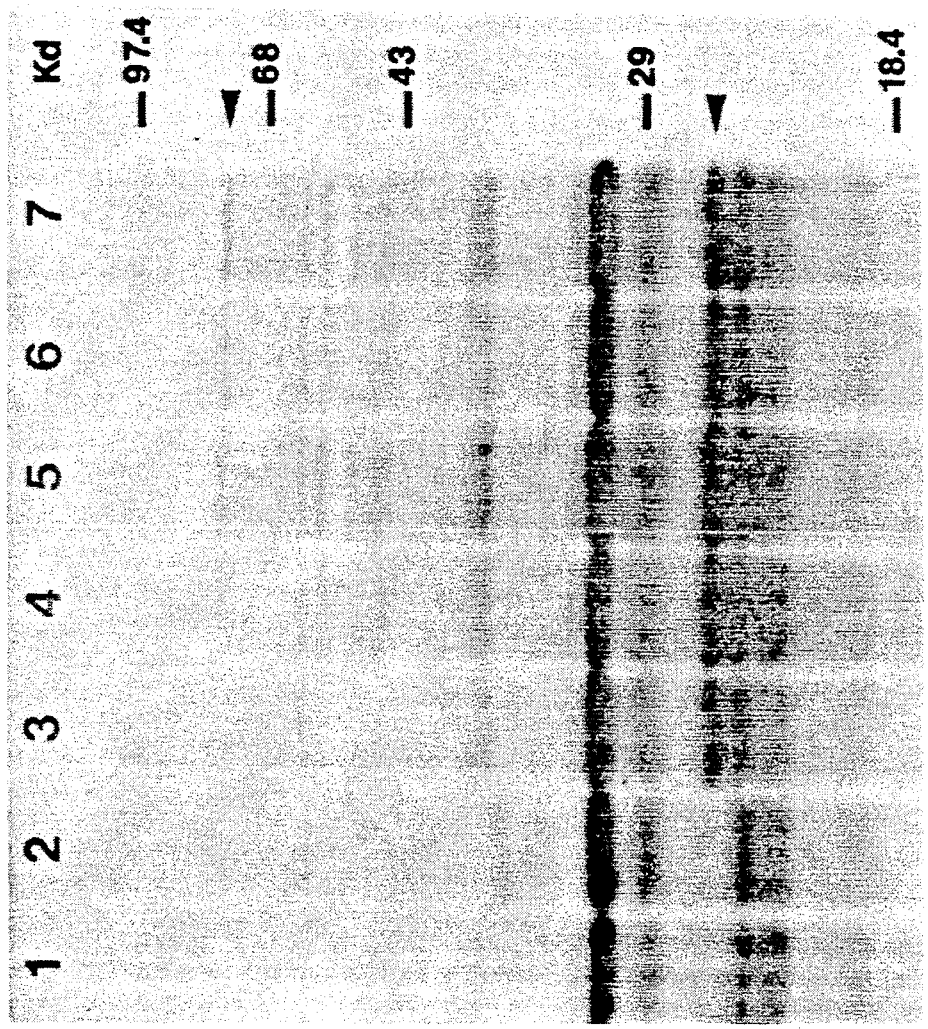
FIGS. 5A and 5B show products of the 2.7 kbp SstI clone in E. coli.

In maxicell experiments, two major proteins were associated with the cloned 2.7 kbp SstI fragment. These were estimated to have molecular weights of 76 and 25.5 kDa (data not shown). The two proteins were also seen when pNFD13-2 and its deletion derivatives were used as templates in an in vitro transcription-translation system. (See FIG. 5A) Appearance of the 76 kDa band coincided with Tc$^r$ expression in *E. coli*. That is, the 76 kDa band was present in deletions that still conferred resistance on *E. coli* (pNFD13-2Δ1, pNFD13-2Δ3), was consistently fainter in the deletion which conferred reduced resistance (pNFD13-2Δ4), and was missing in the Tc$^r$ deletions (pNFD13-2Δ5, pNFD13-2Δ6). By contrast, the 25.5 kDa band was produced from the Tc$^s$ deletions pNFD13-2Δ5 and pNFD13-2Δ6. The Tc$^r$ deletion in pNFD13-2ΔRV resulted in the loss of both of the major proteins associated with the SstI insert. Some additional proteins that were unique to the SstI clone were seen with the in vitro transcription. translation system, but these were also present in the Tc$^s$ deletions pNFD13-2Δ5 and pNFD13-2Δ6. Moreover, these proteins were not seen in the maxicell extracts.

Figure 5B:
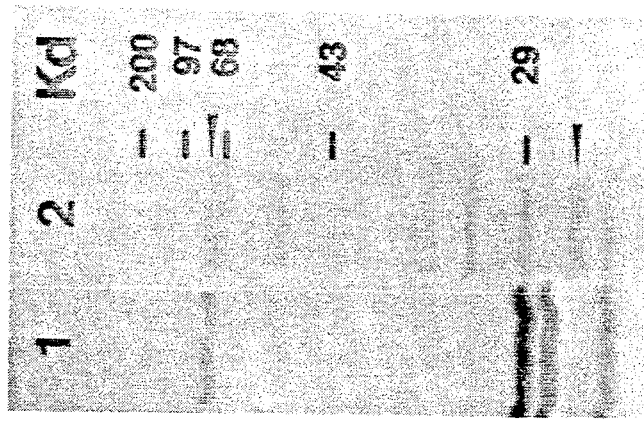

Cellular localization of the 76 kDa band by fractionation of maxicell extracts indicated that this protein partitioned predominately with the soluble fraction. (See FIG. 5B) However, a portion of the protein partitioned with the membrane fraction. The 25.5 kDa band clearly partitioned with the membrane fraction.

4 Relatedness to Other Bacteroides Tetracycline Resistances

Tetracycline resistance has been found to be widespread among strains of colonic Bacteroides. Previous hybridization studies of the Tc$^r$ conjugal elements resident in different Tc$^r$ colonic Bacteroides isolates have revealed extensive DNA hybridization [Shoemaker, et al., *J. Bacteriol.*, 171:1294-1302 (1989)]. To determine if the Tc$^r$ genes in other clinical strains were similar to the Tc$^r$ gene from *B. thetaiotaomicron* DOT, Southern hybridization was performed using the internal 0.9 kbp EcoRI-EcoRV segment of the Tc$^r$ gene to probe chromosomal DNA preparations digested with EcoRV and EcoRI. The Tc$^r$ strains analyzed were clinical isolates of *B. fragilis*, *B. thetaiotaomicron*, *B. uniformis*, *Bacteroides caccae*, and *Bacteroides distasonas* from the continental U.S., Hawaii and Japan. The 0.9 kbp probe hybridized with a 0.9 kbp band in all but one of the Tc$^r$ isolates probed. The only exception to this was *B. distasonas* C30-45, in which the probe hybridized to a fragment much larger than 0.9 kbp. This could be due to the modification or loss of one of the two restriction sites in C30-45. In another *B. distasonas* isolate, 6308, the probe hybridized strongly to a 0.9 kbp band. *B. fragilis* V479 exhibited weak hybridization relative to the other strains, but the cross-hybridizing band was the same 0.9 kbp size as the probe. The probe did not hybridize to DNA from Tc$^s$ type strain controls. These results indicated that the gene cloned in the 2.7 kbp SstI fragment is widespread among clinical isolates of colonic Bacteroides species. Given the stringency used in these experiments, it is estimated that the Tc$^r$ genes found in other Tc$^r$ strains of Bacteroides share at least 80% identity with the Tc$^r$ gene from *B. thetaiotaomicron* DOT.

5. DNA Sequence

The DNA sequence of the 2.7 kbp SstI fragment was obtained. The sequence of the entire fragment is presented in Chart A below.

Only one open reading frame within the SstI clone was sufficiently large to encode a protein of the estimated 76 kDa. (See FIG. 4) All other open reading frames in the fragment were less than 400 bp. The start codon of the large open reading frame was 22 bp to the right of the EcoRI site in FIG. 1 The open reading frame spanned the 0.9 kbp EcoRI-EcoRV region, which was determined to be internal to the Tc$^r$ gene. The location and extent of the open reading frame were also consistent with the exonuclease III deletion results. No additional open reading frames were found that might encode the 25.5 kDa protein seen in maxicells and in vitro transcription-translation. Presumably this protein was produced by a fusion between insert and vector DNA.

The TetQ open reading frame codes for a protein of 642 amino acids (deduced molecular weight, 72,100 Da). The amino acid sequence of the protein is given below in Chart B. The tetQ gene had 40.1 mol % G+C, compared to 42 mol % G+C of the chromosome of *B. thetaiotaomicron*, the species from which the Tc$^r$ gene was cloned [Johnson, *J. Syst. Bacteriol.*, 28:245–256 (1979)].

6. Relatedness to Previously Sequenced Tc$^r$ Proteins

The length of the deduced Bacteroides Tc$^r$ protein was similar to the lengths of proteins encoded by tetM and tetO [Martin, et al., *Nucl. Acids Res.*, 14:7047–7058 (1986); Nesin, et al., *Antimicrob. Agents Chemother.*, in press; Sanchez-Pescador, et al., *Nucl. Acids Res.*, 16:1216–1217 (1988); LeBlanc, et al., *J. Bacteriol.*, 170:3618–3626 (1988); Manavathu, et al., *Gene.* 62:17–26 (1988)], which range from 638 amino acids to 640 amino acids. Comparisons of the Bacteroides Tc$^r$ amino acid sequence to those of TetM and TetO revealed extensive regions of similarity. (See FIGS. 6A and 6B) However, the amino acid sequence of the Bacteroides Tc$^r$ protein was less closely related to the amino acid sequences of TetM and TetO (40.1–40.3% identity) than these sequences are to each other (75.6–76.9% identity; Table 4). In these comparisons, clusters of identity extended over the length of the alignment, but were concentrated in the amino-terminal region. The amino acid sequence of the Bacteroides Tc$^r$ protein had no significant similarity to those of sequenced Tc$^r$ genes belonging either to the efflux or to the tetracycline detoxification classes of resistance. The results of these comparisons indicated the Bacteroides Tc$^r$ gene was likely to be a member of that the ribosome protection class of Tc$^r$, but was clearly in a different hybridization class from TetM and TetO. Accordingly, we have designated this new class TetQ.

A hydrophobicity plot generated from the deduced amino acid sequence of TetQ was very similar to those generated for TetM and TetO. Since TetM and TetO are thought to be soluble proteins that function in the cytoplasm [Burdett, *J. Bacteriol.*, 165:564–569 (1986); Manavathu, et al., *Antimicrob. Agents Chemother.*, 34:71–77 (1990)], this suggests that TetQ is also a soluble protein. However, TetQ contained a relatively hydrophobic internal region (residues 205–247) that was not extant in TetM or TetO. This could explain why a portion of the Bacteroides Tc$^r$ protein fractionated with the membrane in maxicell separations.

7. Upstream Region of tetQ

The DNA sequence of the upstream region of tetQ is shown in FIGS. 7A and 7B. An *E. coli*-like promoter sequence was found immediately upstream of the start of the open reading frame. The deletions in pNFD13.2Δ1 through pNFD13-2Δ3, which did not affect the tetracycline MIC in *E. coli*, left this promoter sequence intact. pNFD13-2Δ4, in which the −35 region of this promoter was deleted, reduced the MIC in *E. coli* pNFD13.2Δ5, in which both the −35 and the −10 region of this promoter were deleted, abolished resistance in *E. coli*. Thus, the *E. coli*-like −10 and −35 regions probably constitute the promoter that is driving transcription in *E. coli*.

Interestingly, this region was not sufficient for expression in Bacteroides, as evidenced by the observation that pNFD13-2Δ3 did not confer resistance on Bacteroides. The largest deletion that was still active in Bacteroides (pNFD13-2Δ2) contained the *E. coli* promoter plus about an additional 150 bp. The sequence of the smallest promoter region identified as functional in Bacteroides species is presented in Chart C below.

The upstream regions of tetM and tetO genes showed remarkable sequence similarity. This region contained the putative Gram-positive ribosome binding site [Martin, et al., *Nucl. Acids Res.*, 14:7047–7058 (1986)]. A comparison of the upstream region of tetM/O to that of tetQ disclosed no detectable similarity. (See FIGS. 6A and 6B) The tetQ upstream region also lacked a distinguishable ribosome binding site.

8. Relatedness to Tc$^r$ of pRRI4

Plasmid pNFD13-2 labeled with P$^{32}$ was used as a probe to hybridize to pRRI4 digested with EcoRI, PvuII, HincII-ECoRV and NciI. Plasmid pRRI4 in *P. ruminicola* 223/M2/7 was obtained from Dr. Harry J. Flint, Rowett Research Institute, Bucksburn, Aberdeen, U.K. It was extracted from *P. ruminicola* 223/M2/7 by standard techniques [Maniatis, et al., supra]. A cross-hybridizing region was identified. To ascertain if this cross-hybridizing region contained the Tc$^r$ gene, a 5 kbp HincII-PvuII segment which covers this region was cloned into pFD160 and mobilized from *E. coli* into *B. uniformis*. The resulting transconjugants were Tc$^r$. Other hybridization experiments also indicated that the Tc$^r$ gene on pRRI4 was at least 80% homologous to the Tc$^r$ genes on pNFD13-2 and other Bacteroides Tc$^r$Em$^r$ elements.

Recently, sequencing of the Tc$^r$ gene on pRRI4 has been completed. Its sequence has been found to be 97% identical to that of the Tc$^r$ gene on pNFD13-2. Accordingly, it is in the TetQ class.

C. Discussion

By size and amino acid sequence similarity, the Bacteroides TetQ appeared to be a ribosome protection type of tetracycline resistance. However, TetQ clearly did not belong in either class TetM or class TetO because the amino acid identity with those classes is only 40.3–40.9%.

All Tc$^r$ Bacteroides strains that we screened had DNA which hybridized to an internal fragment of the cloned Tc$^r$ gene under conditions of high stringency. Thus, TetQ is probably the predominant Tc$^r$ among the colonic Bacteroides. In fact, recent evidence indicates that Tc$^r$ determinants from colonic and oral Bacteroides have high similarity [Guiney and Bouic, *J. Bacteriol.*, 172:495–497 (1990)]. This suggests that TetQ may be ubiquitous in the genus Bacteroides. Also, at least one *P. ruminicola* Tc$^r$ gene is of the TetQ class.

Previously sequenced ribosome protection Tc$^r$ genes were remarkable for their sequence similarity (Table 4). For instance, the TetO found in *Campylobacter jejuni* shared 98.1% intraclass amino acid identity with the TetO found in *Streptococcus mutans*. The *C. jejuni* TetO shared 75.1–76.8% interclass amino acid identity with the TetM's found in Staphylococcus, Streptococcus, and Ureaplasma. Genes that are similar enough to cross-hybridize with tetM and tetO on Southern blots have been found in Clostridium, Eikenella, Fusobacterium, Gardnerella, Hemophilus, Kingella, Mycoplasma, Neisseria, and Veillonella [Salyers, et al., *Mol. Microbiol.*, 4:151–156 (1989)].

The amino-terminal regions of TetM and TetO have high amino acid similarity to the amino-terminal region of the elongation factors [Sanchez-Pescador, et al., *Nucl. Acids Res.*, 16, 1218 (1988); Manavathu et al., *Antimicrob. Agents Chemother.*, 34:71–77 (1990)]. This region is responsible for guanosine nucleotide binding by one elongation factor (EF-Tu) [Jacquet and Parmeggiani, *The EMBO J.*, 7:2861–2867 (1988); Jurnak, *Science*. 230:32–36 (1985)], and is conserved in GTP-binding proteins [Halliday, *J. Nucleotide Prot. Phosphoryl. Res.*, 9:435–448 (1984)]. Though TetQ is the most diverged ribosome protection Tc$^r$, it maintains high amino acid conservation in this GDP/GTP-binding domain. (See FIGS. 6A and 6B) This indicates that this functional domain may be involved directly in the ribosome protection resistance mechanism. Manavathu, et al., *Antimicrob. Agents Chemother.*, 34:71–77 (1990), suggested that TetO may have the potential to bind GTP, but no such binding has yet been demonstrated.

The upstream regions of tetM and tetO genes, which are virtually identical, contain a Gram-positive ribosome binding site. The mol % G+C of tetQ (40.1%) is similar to that of tetM and tetO, but is also similar to the mol % G+C of chromosomal DNA from colonic Bacteroides [39–46%; Johnson, *J. Syst. Bacteriol.*, 28:245–256 (1978)]. By contrast, the upstream region of tetO is completely different from that of tetM and tetO.

TABLE 2

Strains Used In Connection With Sequencing Of Tc$^r$

| Strain or Plasmid | Relevant Phenotype |
|---|---|
| *E. coli* strains | |
| DH5α | RecA Δ(argF-lacA)U169 θ80dlacΔM15 |
| LCD44 | RecA MetE Tc$^s$ derivative of RK5173. |
| Bacteroides strains | |
| *B. thetaoitaomicron* | |
| 5482 | |
| BT4001 | Tc$^s$ Em$^s$; Spontaneous Rif$^r$ derivative of *B. thetaiotaomicron* 5482 |
| BT4002 | Tc$^r$ |
| BT4004 | Tc$^r$ |
| BT4007 | Tc$^r$ Em$^r$ |
| BT4008 | Tc$^r$ Em$^r$ |
| 2808 | Tc$^r$ |
| *B. uniformis* | |

TABLE 2-continued

Strains Used In Connection With Sequencing Of Tc$^r$

| Strain or Plasmid | Relevant Phenotype |
|---|---|
| BU1001 | Tc$^s$; Rif$^r$ derivative of *B. uniformis* 0061 |
| C7-17 | Tc$^r$ |
| 3537 | Tc$^r$ |
| T1-1 | Tc$^r$ |
| *B. distasonas* | |
| 4243 | Tc$^s$ |
| C30-45 | Tc$^r$ |
| 6308 | Tc$^r$ |
| *B. caccae* | |
| 3452A | Tc$^s$ |
| 8608 | Tc$^r$ |
| *B. fragilis* | |
| AK87 | Tc$^r$ |

$^a$Resistance phenotype expressed in *E. coli* is indicated in parenthesis.

TABLE 3

GenBank Access Codes For Sequences

| Source organism | Gene product | GenBank Locus | GenBank Access. |
|---|---|---|---|
| *Staphylococcus aureus* | TetM | Statetm | M21136 |
| *Streptococcus faecalis* | TetM | Str1545tr | X04388 |
| *Ureaplasma urealyticum* | TetM | X06901 | X06901 |
| *Campylobacter jejuni* | TetO | Cajtrccra | M18896 |
| *Streptococcus mutans* | TetO | Stateosm | M20925 |
| *Escherichia coli* | EF-Tu | Ecotgtufb | J01717 |
| | EF-G | Ecostra | X00415 |
| *Micrococcus luteus* | EF-Tu | M17788 | M17788 |
| | EF-G | M17788 | M17788 |
| *Spirulina platensis* | EF-Tu | X15646 | X15646 |
| | EF-G | X15646 | X15646 |
| *Thermus thermophilus* | EF-Tu | Tthtuf1 | X05977 |
| | EF-G | X16278 | X16278 |
| *Thermotoga maritima* | EF-Tu | Tmoeftu | M27479 |
| *Euglena gracilis* chloroplast | EF-Tu | Egrcpeftu | X00044 |
| *Methanococcus vannielii* | EF-1 | Mvatuf | X05698 |
| | EF-2 | Mvafus | X12384 |
| *Saccharomyces cerevisiae* | EF-1α | Yscefla | X00779 |
| *Mucor racemonsus* | EF-1α | Mratefla | J02605 |
| *Dictyostelium discoideum* | EF-2 | Ddief2 | M26017 |
| *Drosophila melanogaster* | EF-2 | X15805 | X15805 |
| *Xenous laevis* | EF-1α | Xelefla1 | M5697 |
| *Mesocricetus* sp. | EF-2 | Hamef2 | M13708 |
| *Mus musculus* | EF-1α | M22432 | M22432 |
| *Rattus norvegicus* | EF-2 | Ratef2r | Y07504 |
| *Homo sapiens* | EF-1α | Humefla | X03558 |
| | EF-2 | Humef2ab | M30456 |

TABLE 4

Percent amino acid similarity and percent amino acid identity between deduced peptide sequences of ribosome protection tetracycline resistance genes

| | percent similarity | | | | | |
|---|---|---|---|---|---|---|
| | 1 | 2 | 3 | 4 | 5 | 6 |
| 1. *S. aureus* TetM | — | 95.3 | 98.1 | 85.3 | 85.9 | 62.5 |
| 2. *S. pneumoniae* TetM | 92.2 | — | 96.7 | 85.7 | 86.1 | 61.1 |
| 3. *U. urealyticum* TetM | 96.6 | 95.0 | — | 85.7 | 86.3 | 62.5 |
| 4. *C. jejuni* TetO | 75.1 | 76.8 | 76.0 | — | 98.4 | 60.5 |
| 5. *S. mutans* TetO | 75.6 | 76.9 | 76.4 | 98.1 | — | 60.8 |
| 6. *B. thetaiotaomicron* TetQ | 41.2 | 41.0 | 41.2 | 41.0 | 41.0 | — | percent identity

Chart A

| | | | | | | | | | | | | |
|---|---|---|---|---|---|---|---|---|---|---|---|---|
| GAGCTCTAAA | TTTAAATATA | AACAACGAAT | TATCTCCTTA | ACGTACGTTT | | | | | | | | 50 |
| TCGTTCCATT | GGCCCTCAAA | CCCCGTTATA | TACATTCATG | TCCATTTATG | | | | | | | | 100 |
| TAAAAAATCC | TGCTGACCTT | GTTTATGTCT | TGTCAGTCAC | CATTTGCAAA | | | | | | | | 150 |
| ACCATATTTG | ACCCTCAAAG | AGGCTGAATT | TGATAAGCAA | CTTGCTACAT | | | | | | | | 200 |
| ACTCATAATA | AGGAGCTAAA | TAGAACACGA | ATGGGAAATA | CTCAAATGCC | | | | | | | | 250 |
| AAACTAAAGA | AGATATTGGC | CAAAATAAAC | GCTATACCGA | GAGAGAAACT | | | | | | | | 300 |
| TGATTTTTCA | ACTTCCTAAA | ACAGTGTTGT | TCAAACATTT | CTACTTATTT | | | | | | | | 350 |
| GTACTTACCA | GTTGAACCTA | CGTTTCCCTA | ATAAAATGTC | TATGGTAAAA | | | | | | | | 400 |
| AGTTAAAAAA | TCCTCCTACT | TTTGTTAGAT | ATATTTTTT | GTGTAATTTT | | | | | | | | 450 |
| GTAATCGTTA | TGCGGCAGTA | ATAATATACA | TATTAATACG | AGTTATTAAT | | | | | | | | 500 |
| CCTGTAGTTC | TCATATGCTA | CGAGGAGGTA | TTAAAAGGTG | CGTTTCGACA | | | | | | | | 550 |

ATGCATCTAT TGTAGTATAT TATTGCTTAA TCCAA ATG AAT ATT ATA    597
                                                           Met Asn Ile Ile

| AAT | TTA | GGA | ATT | CTT | GCT | CAC | ATT | GAT | GCA | GGA | AAA | ACT | TCC | 639 |
|---|---|---|---|---|---|---|---|---|---|---|---|---|---|---|
| Asn | Leu | Gly | Ile | Leu | Ala | His | Ile | Asp | Ala | Gly | Lys | Thr | Ser | |
| 5 | | | | 10 | | | | | 15 | | | | | |

| GTA | ACC | GAG | AAT | CTG | CTG | TTT | GCC | AGT | GGA | GCA | ACG | GAA | AAG | 681 |
|---|---|---|---|---|---|---|---|---|---|---|---|---|---|---|
| Val | Thr | Glu | Asn | Leu | Leu | Phe | Ala | Ser | Gly | Ala | Thr | Glu | Lys | |
| | 20 | | | | 25 | | | | 30 | | | | | |

| TGC | GGC | TGT | GTG | GAT | AAT | GGT | GAC | ACC | ATA | ACG | GAC | TCT | ATG | 723 |
|---|---|---|---|---|---|---|---|---|---|---|---|---|---|---|
| Cys | Gly | Cys | Val | Asp | Asn | Gly | Asp | Thr | Ile | Thr | Asp | Ser | Met | |
| | | 35 | | | | | 40 | | | | | 45 | | |

| GAT | ATA | GAG | AAA | CGT | AGA | GGA | ATT | ACT | GTT | CGG | GCT | TCT | ACG | 765 |
|---|---|---|---|---|---|---|---|---|---|---|---|---|---|---|
| Asp | Ile | Glu | Lys | Arg | Arg | Gly | Ile | Thr | Val | Arg | Ala | Ser | Thr | |
| | | | 50 | | | | | 55 | | | | | 60 | |

| ACA | TCT | ATT | ATC | TGG | AAT | GGT | GTG | AAA | TGC | AAT | ATC | ATT | GAC | 807 |
|---|---|---|---|---|---|---|---|---|---|---|---|---|---|---|
| Thr | Ser | Ile | Ile | Trp | Asn | Gly | Val | Lys | Cys | Asn | Ile | Ile | Asp | |
| | | | | 65 | | | | | 70 | | | | | |

| ACT | CCG | GGA | CAC | ATG | GAT | TTT | ATT | GCG | GAA | GTG | GAG | CGG | ACA | 849 |
|---|---|---|---|---|---|---|---|---|---|---|---|---|---|---|
| Thr | Pro | Gly | His | Met | Asp | Phe | Ile | Ala | Glu | Val | Glu | Arg | Thr | |
| 75 | | | | | 80 | | | | | 85 | | | | |

| TTC | AAA | ATG | CTT | GAT | GGA | GCA | GTC | CTC | ATC | TTA | TCC | GCA | AAG | 891 |
|---|---|---|---|---|---|---|---|---|---|---|---|---|---|---|
| Phe | Lys | Met | Leu | Asp | Gly | Ala | Val | Leu | Ile | Leu | Ser | Ala | Lys | |
| | 90 | | | | 95 | | | | | 100 | | | | |

| GAA | GGC | ATA | CAA | GCG | CAG | ACA | AAG | TTG | CTG | TTC | AAT | ACT | TTA | 933 |
|---|---|---|---|---|---|---|---|---|---|---|---|---|---|---|
| Glu | Gly | Ile | Gln | Ala | Gln | Thr | Lys | Leu | Leu | Phe | Asn | Thr | Leu | |
| | | 105 | | | | 110 | | | | | 115 | | | |

| CAG | AAG | CTG | CAA | ATC | CCG | ACA | ATT | ATA | TTT | ATC | AAT | AAG | ATT | 975 |
|---|---|---|---|---|---|---|---|---|---|---|---|---|---|---|
| Gln | Lys | Leu | Gln | Ile | Pro | Thr | Ile | Ile | Phe | Ile | Asn | Lys | Ile | |
| | | | 120 | | | | | 125 | | | | | 130 | |

| GAC | CGA | GCC | GGT | GTG | AAT | TTG | GAG | CGT | TTG | TAT | CTG | GAT | ATA | 1017 |
|---|---|---|---|---|---|---|---|---|---|---|---|---|---|---|
| Asp | Arg | Ala | Gly | Val | Asn | Leu | Glu | Arg | Leu | Tyr | Leu | Asp | Ile | |
| | | | | 135 | | | | | 140 | | | | | |

| AAA | GCA | AAT | CTG | TCT | CAA | GAT | GTC | CTG | TTT | ATG | CAA | AAT | GTT | 1059 |
|---|---|---|---|---|---|---|---|---|---|---|---|---|---|---|
| Lys | Ala | Asn | Leu | Ser | Gln | Asp | Val | Leu | Phe | Met | Gln | Asn | Val | |
| 145 | | | | 150 | | | | | | 155 | | | | |

| GTC | GAT | GGA | TCG | GTT | TAT | CCG | GTT | TGC | TCC | CAA | ACA | TAT | ATA | 1101 |
|---|---|---|---|---|---|---|---|---|---|---|---|---|---|---|
| Val | Asp | Gly | Ser | Val | Tyr | Pro | Val | Cys | Ser | Gln | Thr | Tyr | Ile | |
| | 160 | | | | | 165 | | | | | 170 | | | |

| AAG | GAA | GAA | TAC | AAA | GAA | TTT | GTA | TGC | AAC | CAT | GAC | GAC | AAT | 1143 |
|---|---|---|---|---|---|---|---|---|---|---|---|---|---|---|
| Lys | Glu | Glu | Tyr | Lys | Glu | Phe | Val | Cys | Asn | His | Asp | Asp | Asn | |
| | | 175 | | | | | 180 | | | | | 185 | | |

| ATA | TTA | GAA | CGA | TAT | TTG | GCG | GAT | AGC | GAA | ATT | TCA | CCG | GCT | 1185 |
|---|---|---|---|---|---|---|---|---|---|---|---|---|---|---|
| Ile | Leu | Glu | Arg | Tyr | Leu | Ala | Asp | Ser | Glu | Ile | Ser | Pro | Ala | |
| | | | 190 | | | | | 195 | | | | | 200 | |

Chart A -continued

| | | | | | | | | | | | | | | |
|---|---|---|---|---|---|---|---|---|---|---|---|---|---|---|
| GAT Asp | TAT Tyr | TGG Trp | AAT Asn | ACG Thr 205 | ATA Ile | ATC Ile | GCT Ala | CTT Leu | GTG Val 210 | GCA Ala | AAA Lys | GCC Ala | AAA Lys | 1227 |
| GTC Val 215 | TAT Tyr | CCG Pro | GTG Val | CTA Leu | CAT His 220 | GGA Gly | TCA Ser | GCA Ala | ATG Met | TTC Phe 225 | AAT Asn | ATC Ile | GGT Gly | 1269 |
| ATC Ile | AAT Asn 230 | GAG Glu | TTG Leu | TTG Leu | GAC Asp | GCC Ala 235 | ATC Ile | ACT Thr | TCT Ser | TTT Phe | ATA Ile 240 | CTT Leu | CCT Pro | 1311 |
| CCG Pro | GCA Ala | TCG Ser 245 | GTC Val | TCA Ser | AAC Asn | AGA Arg | CTT Leu 250 | TCA Ser | TCT Ser | TAT Tyr | CTT Leu | TCT Ser 255 | AAG Lys | 1353 |
| ATA Ile | GAG Glu | CAT His | GAC Asp 260 | CCC Pro | AAA Lys | GGA Gly | CAT His | AAA Lys 265 | AGA Arg | AGT Ser | TTT Phe | CTA Leu | AAA Lys 270 | 1395 |
| ATA Ile | ATT Ile | GAC Asp | GGA Gly | AGT Ser 275 | CTG Leu | AGA Arg | CTT Leu | CGA Arg | GAC Asp 280 | GTT Val | GTA Val | AGA Arg | ATC Ile | 1437 |
| AAC Asn 285 | GAT Asp | TCG Ser | GAA Glu | AAA Lys | TTC Phe 290 | ATC Ile | AAG Lys | ATT Ile | AAA Lys | AAT Asn 295 | CTA Leu | AAA Lys | ACT Thr | 1479 |
| ATC Ile | AAT Asn 300 | CAG Gln | GGC Gly | AGA Arg | GAG Glu | ATA Ile 305 | AAT Asn | GTT Val | GAT Asp | GAA Glu | GTG Val 310 | GGC Gly | GCC Ala | 1521 |
| AAT Asn | GAT Asp | ATC Ile 315 | GCG Ala | ATT Ile | GTA Val | GAG Glu | GAT Asp 320 | ATG Met | GAT Asp | GAT Asp | TTT Phe | CGA Arg 325 | ATC Ile | 1563 |
| GGA Gly | AAT Asn | TAT Tyr | TTA Leu 330 | GGT Gly | GCT Ala | GAA Glu | CCT Pro | TGT Cys 335 | TTG Leu | ATT Ile | CAA Gln | GGA Gly | TTA Leu 340 | 1605 |
| TCG Ser | CAT His | CAG Gln | CAT His | CCC Pro 345 | GCT Ala | CTC Leu | AAA Lys | TCC Ser | TCC Ser 350 | GTC Val | CGG Arg | CCA Pro | GAC Asp | 1647 |
| AGG Arg 355 | CCC Pro | GAA Glu | GAG Glu | AGA Arg | AGC Ser 360 | AAG Lys | GTG Val | ATA Ile | TCC Ser | GCT Ala 365 | CTG Leu | AAT Asn | ACA Thr | 1689 |
| TTG Leu | TGG Trp 370 | ATT Ile | GAA Glu | GAC Asp | CCG Pro | TCT Ser 375 | TTG Leu | TCC Ser | TTT Phe | TCC Ser | ATA Ile 380 | AAC Asn | TCA Ser | 1731 |
| TAT Tyr | AGT Ser | GAT Asp 385 | GAA Glu | TTG Leu | GAA Glu | ATC Ile | TCG Ser 390 | TTA Leu | TAT Tyr | GGT Gly | TTA Leu | ACC Thr 395 | CAA Gln | 1773 |
| AAG Lys | GAA Glu | ATC Ile | ATA Ile 400 | CAG Gln | ACA Thr | TTG Leu | CTG Leu | GAA Glu 405 | GAA Glu | CGA Arg | TTT Phe | TCC Ser | GTA Val 410 | 1815 |
| AAG Lys | GTC Val | CAT His | TTT Phe | GAT Asp 415 | GAG Glu | ATC Ile | AAG Lys | ACT Thr | ATA Ile 420 | TAC Tyr | AAA Lys | GAA Glu | GGA Arg | 1857 |
| CCT Pro 425 | GTA Val | AAA Lys | AAG Lys | GTC Val | AAT Asn 430 | AAG Lys | ATT Ile | TAA Ile | CAG Gln | ATC Ile 435 | GAA Glu | GTG Val | CCG Pro | 1899 |
| CCC Pro | AAC Asn 440 | CCT Pro | TAT Tyr | TGG Trp | GCC Ala | ACA Thr 445 | ATA Ile | GGG Gly | CTG Leu | ACT Thr | CTT Leu 450 | GAT Asp | CCC Pro | 1941 |
| TTA Leu | CCG Pro | TTA Leu 455 | GGG Gly | ACA Thr | GGG Gly | TTG Leu | CAA Gln 460 | ATC Ile | GAA Glu | AGT Ser | GAC Asp | ATC Ile 465 | TCC Ser | 1983 |
| TAT Tyr | GGT Gly | TAT Tyr | CTG Leu 470 | AAC Asn | CAT His | TCT Ser | TTT Phe | CAA Gln 475 | AAT Asn | GCC Ala | GTT Val | TTT Phe | GAA Glu 480 | 2025 |

-continued
Chart A

| | | | | | | | | | | | | | |
|---|---|---|---|---|---|---|---|---|---|---|---|---|---|
| GGG | ATT | CGT | ATG | TCT | TGC | CAA | TCC | GGG | TTA | CAT | GGA | TGG | GAA | 2067
| Gly | Ile | Arg | Met | Ser | Cys | Gln | Ser | Gly | Leu | His | Gly | Trp | Glu |
| | | | 485 | | | | 490 | | | | | | |

GTG ACT GAT CTG AAA GTA ACT TTT ACT CAA GCC GAG TAT TAT 2109
Val Thr Asp Leu Lys Val Thr Phe Thr Gln Ala Glu Tyr Tyr
495                     500                     505

AGC CCG GTA AGT ACA CCT GCT GAT TTC AGA CAG CTG ACC CCT 2151
Ser Pro Val Ser Thr Pro Ala Asp Phe Arg Gln Leu Thr Pro
    510                     515                     520

TAT GTC TTC AGG CTG GCC TTG CAA CAG TCA GGT GTG GAC ATT 2193
Tyr Val Phe Arg Leu Ala Leu Gln Gln Ser Gly Val Asp Ile
        525                     530                     535

CTC GAA CCG ATG CTC TAT TTT GAG TTG CAG ATA CCC CAA GCG 2235
Leu Glu Pro Met Leu Tyr Phe Glu Leu Gln Ile Pro Gln Ala
            540                     545                     550

GCA AGT TCC AAA GCT ATT ACA GAT TTG CAA AAA ATG ATG TCT 2277
Ala Ser Ser Lys Ala Ile Thr Asp Leu Gln Lys Met Met Ser
                555                     560

GAG ATT GAA GAC ATC AGT TGC AAT AAT GAG TGG TGT CAT ATT 2319
Glu Ile Glu Asp Ile Ser Cys Asn Asn Glu Trp Cys His Ile
565                     570                     575

AAA GGG AAA GTT CCA TTA AAT ACA AGT AAA GAC TAT GCA TAC 2361
Lys Gly Lys Val Pro Leu Asn Thr Ser Lys Asp Tyr Ala Ser
    580                     585                     590

GAA GTA AGT TCA TAC ACT AAG GGC TTA GGC ATT TTT ATG GTT 2403
Glu Val Ser Ser Tyr Thr Lys Gly Leu Gly Ile Phe Met Val
        595                     600                     605

AAG CCA TGC GGG TAT CAA ATA ACA AAA GGC GGT TAT TCT GAT 2445
Lys Pro Cys Gly Tyr Gln Ile Thr Lys Gly Gly Tyr Ser Asp
            610                     615                     620

AAT ATC CGC ATG AAC GAA AAA GAT AAA CTT TTA TTC ATG TTC 2487
Asn Ile Arg Met Asn Glu Lys Asp Lys Leu Leu Phe Met Phe
                625                     630

CAA AAA TCA ATG TCA TCA AAA TAATGGAGCG GTCAGGAAAT 2528
Gln Lys Ser Met Ser Ser Lys
635                 640

TTCTATAAGG CAATACAGTT GGGATATATA CTTATCTCCA TTCTTATCGG 2578

ATGTATGGCA TATAATAGCC TCTATGAATG GCAGGAGATA GAAGCATTAG 2628

AACTTGGCAA TAAAAAAATA GACGAGCTC 2657
(SEQ ID NO: 2)

Chart B

Met Asn Ile Ile Asn Leu Gly Ile Leu Ala His Ile (SEQ ID NO:3)
                5                   10                  15

Lys Thr Ser Val Thr Glu Asn Leu Leu Phe Ala Ser Gly Ala Thr
            20                  25                  30

Glu Lys Cys Gly Cys Val Asp Asn Gly Asp Thr Ile Thr Asp Ser
            35                  40                  45

Met Asp Ile Glu Lys Arg Arg Gly Ile Thr Val Arg Ala Ser Thr
            50                  55                  60

Thr Ser Ile Ile Trp Asn Gly Val Lys Cys Asn Ile Ile Asp Thr
            65                  70                  75

Pro Gly His Met Asp Phe Ile Ala Glu Val Glu Arg Thr Phe Lys
            80                  85                  90

Met Leu Asp Gly Ala Val Leu Ile Leu Ser Ala Lys Glu Gly Ile
            95                  100                 105

-continued
Chart B

Gln Ala Gln Thr Lys Leu Leu Phe Asn Thr Leu Gln Lys Leu Gln
            110                 115                 120

Ile Pro Thr Ile Ile Phe Ile Asn Lys Ile Asp Arg Ala Gly Val
            125                 130                 135

Asn Leu Glu Arg Leu Tyr Leu Asp Ile Lys Ala Asn Leu Ser Gln
            140                 145                 150

Asp Val Leu Phe Met Gln Asn Val Val Asp Gly Ser Val Tyr Pro
            155                 160                 165

Val Cys Ser Gln Thr Tyr Ile Lys Glu Tyr Lys Glu Phe Val
            170                 175                 180

Cys Asn His Asp Asp Asn Ile Leu Glu Arg Tyr Leu Ala Asp Ser
            185                 190                 195

Glu Ile Ser Pro Ala Asp Tyr Trp Asn Thr Ile Ile Ala Leu Val
            200                 205                 210

Chart B (continued)

Ala Lys Ala Lys Val Tyr Pro Val Leu His Gly Ser Ala Met Phe
215                        220                       225

Asn Ile Gly Ile Asn Glu Leu Leu Asp Ala Ile Thr Ser Phe Ile
230                       235                      240

Leu Pro Pro Ala Ser Val Ser Asn Arg Leu Ser Ser Tyr Leu Tyr
245                       250                      255

Lys Ile Glu His Asp Pro Lys Gly His Lys Arg Ser Phe Leu Lys
260                       265                      270

Ile Ile Asp Gly Ser Leu Arg Leu Arg Asp Val Val Arg Ile Asn
275                       280                      285

Asp Ser Glu Lys Phe Ile Lys Ile Lys Asn Leu Lys Thr Ile Asn
290                       295                      300

Gln Gly Arg Glu Ile Asn Val Asp Glu Val Gly Ala Asn Asp Ile
305                       310                      315

Ala Ile Val Glu Asp Met Asp Asp Phe Arg Ile Gly Asn Tyr Leu
320                       325                      330

Gly Ala Glu Pro Cys Leu Ile Gln Gly Leu Ser His Gln His Pro
335                       340                      345

Ala Leu Lys Ser Ser Val Arg Pro Asp Arg Pro Glu Glu Arg Ser
350                       355                      360

Lys Val Ile Ser Ala Leu Asn Thr Leu Trp Ile Glu Asp Pro Ser
365                       370                      375

Leu Ser Phe Ser Ile Asn Ser Tyr Ser Asp Glu Leu Glu Ile Ser
380                       385                      390

Leu Tyr Gly Leu Thr Gln Lys Glu Ile Ile Gln Thr Leu Leu Glu
395                       400                      405

Glu Arg Phe Ser Val Lys Val His Phe Asp Glu Ile Lys Thr Ile
410                       415                      420

Tyr Lys Glu Arg Pro Val Lys Lys Val Asn Lys Ile Ile Gln Ile
425                       430                      435

Glu Val Pro Pro Asn Pro Tyr Trp Ala Thr Ile Gly Leu Thr Leu
440                       445                      450

Glu Pro Leu Pro Leu Gly Thr Gly Leu Gln Ile Glu Ser Asp Ile
455                       460                      465

Ser Tyr Gly Tyr Leu Asn His Ser Phe Gln Asn Ala Val Phe Glu
470                       475                      480

Gly Ile Arg Met Ser Cys Gln Ser Gly Leu His Gly Trp Glu Val
485                       490                      495

Thr Asp Leu Lys Val Thr Phe Thr Gln Ala Glu Tyr Tyr Ser Pro
500                       505                      510

Val Ser Tyr Pro Ala Asp Phe Arg Gln Leu Thr Pro Tyr Val Phe
515                       520                      525

Arg Leu Ala Leu Gln Gln Ser Gly Val Asp Ile Leu Glu Pro Met
530                       535                      540

Leu Tyr Phe Glu Leu Gln Ile Pro Gln Ala Ala Ser Ser Lys Ala
545                       550                      555

Ile Thr Asp Leu Gln Lys Met Met Ser Glu Ile Glu Asp Ile Ser
560                       565                      570

Cys Asn Asn Glu Trp Cys His Ile Lys Gly Lys Val Pro Leu Asn
575                       580                      585

Thr Ser Lys Asp Tyr Ala Ser Glu Val Ser Ser Tyr Thr Lys Gly
590                       595                      600

Leu Gly Ile Phe Met Val Lys Pro Cys Gly Tyr Gln Ile Thr Lys
605                       610                      615

Gly Gly Tyr Ser Asp Asn Ile Arg Met Asn Glu Lys Asp Lys Leu
620                       625                      630

Leu Phe Met Phe Gln Lys Ser Met Ser Ser Lys
635                       640

Chart C

```
AAAAATCCTC CTACTTTTGT TAGATATATT TTTTTGTGTA ATTTTGTAAT    50
CGTTATGCGG CAGTAATAAT ATACATATTA ATACGAGTTA TTAATCCTGT   100
AGTTCTCATA TGCTACGAGG AGGTATTAAA AGGTGCGTTT CGACAATGCA   150
TCTATTGTAG TATATTATTG CTTAATCCAA,                        180
```

---

We claim:

1. A method of introducing heterologous DNA into a *Prevotella ruminicola*, comprising:
   (a) transforming an *Escherichia coli* with a shuttle vector comprising:
   (i) a mobilization region which permits transfer of the shuttle vector from *Escherichia coli* to a colonic Bacteroides species;
   (ii) a mobilization region which permits transfer of the shuttle vector from the colonic Bacteroides species to the *P. ruminicola*: and
   (iii) the heterologous DNA operatively linked to a promoter functional in the *P. ruminicola*:
   (b) contacting the *E. coli* with a colonic Bacteroides species under conditions sufficient so that the shuttle vector is transferred from the *E. coli* to the colonic Bacteroides species; and
   (c) contacting the colonic Bacteroides species with the *P. ruminicola* under conditions sufficient so that the shuttle vector is transferred from the colonic Bacteroides species to the *P. ruminicola*.

2. The method of claim 1 wherein the colonic Bacteroides species contains the Tc$^r$Em$^r$ 12256 element.

3. The method of claim 1 wherein the colonic Bacteroides species is *Bacteroides uniformis*.

4. The method of claim 1 wherein the shuttle vector is pRDB5.

5. The method of claim 1 wherein the *P. ruminicola* is *P. ruminicola* B$_1$4.

6. The method of claim 1 wherein the promoter comprises the following sequence (SEQ ID NO:1):

```
AAAAATCCTC CTACTTTTGT TAGATATATT TTTTGTGTA ATTTTGTAAT    50
CGTTATGCGG CAGTAATAAT ATACATATTA ATACGAGTTA TTAATCCTGT  100
AGTTCTCATA TGCTACGAGG AGGTATTAAA AGGTGCGTTT CGACAATGCA  150
TCTATTGTAG TATATTATTG CTTAATCCAA                        180.
```

7. The *P. ruminicola* produced by the method of any one of claims 1-6.

8. A shuttle vector comprising:
   a mobilization region which permits transfer of the shuttle vector from *Escherichia coli* to a colonic Bacteroides species;
   a mobilization region which permits transfer of the shuttle vector from the colonic Bacteroides species to a *Prevotella ruminicola*; and
   heterologous DNA operatively linked to a promoter functional in *P. ruminicola*.

9. The shuttle vector of claim 8 which is pRDB5.

10. The shuttle vector of claim 8 wherein the promoter comprises the following sequence (SEQ ID NO:1):

```
AAAAATCCTC CTACTTTTGT TAGATATATT TTTTGTGTA ATTTTGTAAT    50
CGTTATGCGG CAGTAATAAT ATACATATTA ATACGAGTTA TTAATCCTGT  100
AGTTCTCATA TGCTACGAGG AGGTATTAAA AGGTGCGTTT CGACAATGCA  150
TCTATTGTAG TATATTATTG CTTAATCCAA                        180.
```

11. *Prevotella ruminicola* containing the shuttle vector of claim 8, 9 or 10.

12. The *P. ruminicola* of claim 11 which is *P. ruminicola* B$_1$4.

* * * * *

UNITED STATES PATENT AND TRADEMARK OFFICE
CERTIFICATE OF CORRECTION

PATENT NO. : 5,322,784
DATED : June 21, 1994
INVENTOR(S) : Abigail A. Salyers et al.

It is certified that error appears in the above-indentified patent and that said Letters Patent is hereby corrected as shown below:

Column 1, line 31, after "Bacteroides" insert --species.--.

Column 3, line 18, after "desirable" insert --.--.

Column 4, line 4, after "*ruminicola*" delete ":" and insert --;--.

Column 5, line 23, delete "transcription. translation" and substitute --transcription-translation--.

Column 5, line 58, delete "tetQ" and "tetQ" and substitute --*tetQ*-- and --*tetQ*--.

Column 5, line 59, delete "tetM" and substitute --*tetM*--.

Column 5, line 61, delete "tetO" and substitute --*tetO*--.

Column 5, line 64, delete "tetM" and substitute --*tetM*--; delete "tetO" and substitute --*tetO*--.

Column 8, line 42, delete "Tc$^r$Enm$^r$" and substitute --Tc$^r$Em$^r$--.

Column 8, line 68, delete "sections" and substitute --selections--.

UNITED STATES PATENT AND TRADEMARK OFFICE
CERTIFICATE OF CORRECTION

PATENT NO. : 5,322,784
DATED : June 21, 1994
INVENTOR(S) : Abigail A. Salyers et al.

It is certified that error appears in the above-indentified patent and that said Letters Patent is hereby corrected as shown below:

Column 10, line 14, delete second "A".

Column 10, line 26, delete "TN4351" and substitute --TN$\underline{4351}$--.

Column 10, line 27, delete "626.632" and substitue --626-632--.

Column 10, line 47, delete "TN4351" and substitute --TN$\underline{4351}$--.

Column 10, line 56, delete "TN1000" and substitute --TN$\underline{1000}$--.

Column 10, line 59, delete "TN1000" and substitute --TN$\underline{1000}$--.

Column 10, line 60, delete "TN1000" and substitute --TN$\underline{1000}$--.

Column 10, line 64, delete "TN1000" and substitute --TN$\underline{1000}$--.

Column 10, line 65, delete "TN1000" and substitute --TN$\underline{1000}$--.

Column 11, line 6, delete "13.2" and substitute --13-2--.

Column 14, line 2, delete "rifampioin" and substitute --rifampicin--.

Column 15, line 16, delete "TcEm$^r$" and substitute --Tc$^r$Em$^r$--.

UNITED STATES PATENT AND TRADEMARK OFFICE
CERTIFICATE OF CORRECTION

PATENT NO. : 5,322,784
DATED : June 21, 1994
INVENTOR(S) : Abigail A. Salyers et al.

It is certified that error appears in the above-indentified patent and that said Letters Patent is hereby corrected as shown below:

Column 16, line 33, delete "n" and substitute --in--.

Column 16, line 42, delete "TetM" and substitute --_TetM_--; delete "TetO" and substitute --_TetO_--.

Column 16, line 46, delete "TetM" and substitute --_TetM_--; delete "TetO" and substitute --_TetO_--.

Column 16, line 61, delete "2537" and substitute --3537--.

Column 18, line 41, delete "13.2" and substitute --13-2--.

Column 18, line 50, after "kit" insert --(U.S.--.

Column 19, line 3, delete "lac" and substitute --_lac_--.

Column 19, line 26, delete "lac" and substitute --_lac_--.

Column 20, line 16, delete "Tc$^r$" and substitute --Tc$^s$--.

Column 20, line 18, delete "Tc$^r$" and substitute --Tc$^s$--.

Column 20, line 22, delete "transcription. translation" and substitute --transcription-translation--.

Column 22, line 8, delete "13.2" and substitute --13-2--.

Column 22, line 12, delete "13.2" and substitute --13-2--.

Column 22, line 25, delete "tetM" and substitute --_tetM_--; delete "tetO" and substitute --_tetO_--.

UNITED STATES PATENT AND TRADEMARK OFFICE
CERTIFICATE OF CORRECTION

PATENT NO. : 5,322,784
DATED : June 21, 1994
INVENTOR(S) : Abigail A. Salyers et al.

It is certified that error appears in the above-indentified patent and that said Letters Patent is hereby corrected as shown below:

Column 22, line 29, delete "tetM/O" and substitute --*tet*M/O--.

Column 22, line 30, delete "tetQ" and substitute --*tet*Q--.

Column 22, line 31, delete "tetQ" and substitute --*tet*Q--.

Column 23, line 12, delete "tetM" and substitute --*tet*M--; delete "tetO" and substitute --*tet*O--.

Column 23, line 38, delete "tetM" and substitute --*tet*M--; delete "tetO" and substitute --*tet*O--.

Column 23, line 41, delete "tetM" and substitute --*tet*M--; delete "tetO" and substitute --*tet*O--.

Column 23, line 46, delete "tetO" and substitute --*tet*Q--.

Column 23, line 55, delete "argF-lac" and substitute --*argF*lac--.

Column 23, line 56, delete "lac" and substitute --*lac*--.

Column 24, line 47, delete "M5697" and substitute --M25697--.

UNITED STATES PATENT AND TRADEMARK OFFICE
CERTIFICATE OF CORRECTION

PATENT NO. : 5,322,784
DATED : June 21, 1994
INVENTOR(S) : Abigail A. Salyers et al.

It is certified that error appears in the above-indentified patent and that said Letters Patent is hereby corrected as shown below:

IN THE CLAIMS

Col. 51, Claim 1, line 10, delete ":" and substitute --;--.

Claim 1, line 12, delete ":" and substitute --;--.

Col. 52, Claim 6, line 6, at the end of the sequence insert --.--

Claim 10, line 7, at the end of the sequence insert --.--

Signed and Sealed this

Seventeenth Day of September, 1996

Attest:

BRUCE LEHMAN

Attesting Officer    Commissioner of Patents and Trademarks

SEQUENCE LISTING ( 1 ) GENERAL INFORMATION:

( i i i ) NUMBER OF SEQUENCES: 5

( 2 ) INFORMATION FOR SEQ ID NO:1:

( i ) SEQUENCE CHARACTERISTICS:
        ( A ) LENGTH: 180 base pairs
        ( B ) TYPE: nucleic acid
        ( C ) STRANDEDNESS: double stranded
        ( D ) TOPOLOGY: circular ( x i ) SEQUENCE DESCRIPTION: SEQ ID NO:1:

```
AAAAATCCTC  CTACTTTTGT  TAGATATATT  TTTTTGTGTA  ATTTTGTAAT    50

CGTTATGCGG  CAGTAATAAT  ATACATATTA  ATACGAGTTA  TTAATCCTGT   100

AGTTCTCATA  TGCTACGAGG  AGGTATTAAA  AGGTGCGTTT  CGACAATGCA   150

TCTATTGTAG  TATATTATTG  CTTAATCCAA                           180
```

( 2 ) INFORMATION FOR SEQ ID NO:2:

( i ) SEQUENCE CHARACTERISTICS:
        ( A ) LENGTH: 2657 base pairs
        ( B ) TYPE: nucleic acid
        ( C ) STRANDEDNESS: double stranded
        ( D ) TOPOLOGY: circular ( x i ) SEQUENCE DESCRIPTION: SEQ ID NO:2:

```
GAGCTCTAAA TTTAAATATA AACAACGAAT TATCTCCTTA ACGTACGTTT      50

TCGTTCCATT GGCCCTCAAA CCCCGTTATA TACATTCATG TCCATTTATG     100

TAAAAAATCC TGCTGACCTT GTTTATGTCT TGTCAGTCAC CATTTGCAAA     150

ACCATATTTG ACCCTCAAAG AGGCTGAATT TGATAAGCAA CTTGCTACAT     200

ACTCATAATA AGGAGCTAAA TAGAACACGA ATGGGAAATA CTCAAATGCC     250

AAACTAAAGA AGATATTGGC CAAAATAAAC GCTATACCGA GAGAGAAACT     300

TGATTTTTCA ACTTCCTAAA ACAGTGTTGT TCAAACATTT CTACTTATTT     350

GTACTTACCA GTTGAACCTA CGTTTCCCTA ATAAATGTC TATGGTAAAA      400

AGTTAAAAAA TCCTCCTACT TTTGTTAGAT ATATTTTTT GTGTAATTTT      450

GTAATCGTTA TGCGGCAGTA ATAATATACA TATTAATACG AGTTATTAAT     500

CCTGTAGTTC TCATATGCTA CGAGGAGGTA TTAAAAGGTG CGTTTCGACA     550

ATGCATCTAT TGTAGTATAT TATTGCTTAA TCCAA ATG AAT ATT ATA     597
                                       Met Asn Ile Ile
AAT TTA GGA ATT CTT GCT CAC ATT GAT GCA GGA AAA ACT TCC    639
Asn Leu Gly Ile Leu Ala His Ile Asp Ala Gly Lys Thr Ser
 5              10                  15

GTA ACC GAG AAT CTG CTG TTT GCC AGT GGA GCA ACG GAA AAG    681
Val Thr Glu Asn Leu Leu Phe Ala Ser Gly Ala Thr Glu Lys
    20              25                  30

TGC GGC TGT GTG GAT AAT GGT GAC ACC ATA ACG GAC TCT ATG    723
Cys Gly Cys Val Asp Asn Gly Asp Thr Ile Thr Asp Ser Met
        35              40                  45

GAT ATA GAG AAA CGT AGA GGA ATT ACT GTT CGG GCT TCT ACG    765
Asp Ile Glu Lys Arg Arg Gly Ile Thr Val Arg Ala Ser Thr
            50              55                  60

ACA TCT ATT ATC TGG AAT GGT GTG AAA TGC AAT ATC ATT GAC    807
Thr Ser Ile Ile Trp Asn Gly Val Lys Cys Asn Ile Ile Asp
                65              70

ACT CCG GGA CAC ATG GAT TTT ATT GCG GAA GTG GAG CGG ACA    849
Thr Pro Gly His Met Asp Phe Ile Ala Glu Val Glu Arg Thr
 75             80                  85

TTC AAA ATG CTT GAT GGA GCA GTC CTC ATC TTA TCC GCA AAG    891
Phe Lys Met Leu Asp Gly Ala Val Leu Ile Leu Ser Ala Lys
    90              95                 100

GAA GGC ATA CAA GCG CAG ACA AAG TTG CTG TTC AAT ACT TTA    933
Glu Gly Ile Gln Ala Gln Thr Lys Leu Leu Phe Asn Thr Leu
       105              110                 115

CAG AAG CTG CAA ATC CCG ACA ATT ATA TTT ATC AAT AAG ATT    975
Gln Lys Leu Gln Ile Pro Thr Ile Ile Phe Ile Asn Lys Ile
           120              125                 130

GAC CGA GCC GGT GTG AAT TTG GAG CGT TTG TAT CTG GAT ATA   1017
Asp Arg Ala Gly Val Asn Leu Glu Arg Leu Tyr Leu Asp Ile
               135                 140

AAA GCA AAT CTG TCT CAA GAT GTC CTG TTT ATG CAA AAT GTT   1059
Lys Ala Asn Leu Ser Gln Asp Val Leu Phe Met Gln Asn Val
145                 150                 155

GTC GAT GGA TCG GTT TAT CCG GTT TGC TCC CAA ACA TAT ATA   1101
Val Asp Gly Ser Val Tyr Pro Val Cys Ser Gln Thr Tyr Ile
```

|     |     |     |     |     |     |     |     |     |     |     |     |     |     |      |
|-----|-----|-----|-----|-----|-----|-----|-----|-----|-----|-----|-----|-----|-----|------|
|     |     |     | 160 |     |     |     | 165 |     |     |     | 170 |     |     |      |
| AAG | GAA | GAA | TAC | AAA | GAA | TTT | GTA | TGC | AAC | CAT | GAC | GAC | AAT | 1143 |
| Lys | Glu | Glu | Tyr | Lys | Glu | Phe | Val | Cys | Asn | His | Asp | Asp | Asn |      |
|     |     | 175 |     |     |     | 180 |     |     |     |     | 185 |     |     |      |
| ATA | TTA | GAA | CGA | TAT | TTG | GCG | GAT | AGC | GAA | ATT | TCA | CCG | GCT | 1185 |
| Ile | Leu | Glu | Arg | Tyr | Leu | Ala | Asp | Ser | Glu | Ile | Ser | Pro | Ala |      |
|     |     |     | 190 |     |     |     |     | 195 |     |     |     |     | 200 |      |
| GAT | TAT | TGG | AAT | ACG | ATA | ATC | GCT | CTT | GTG | GCA | AAA | GCC | AAA | 1227 |
| Asp | Tyr | Trp | Asn | Thr | Ile | Ile | Ala | Leu | Val | Ala | Lys | Ala | Lys |      |
|     |     |     |     | 205 |     |     |     |     | 210 |     |     |     |     |      |
| GTC | TAT | CCG | GTG | CTA | CAT | GGA | TCA | GCA | ATG | TTC | AAT | ATC | GGT | 1269 |
| Val | Tyr | Pro | Val | Leu | His | Gly | Ser | Ala | Met | Phe | Asn | Ile | Gly |      |
| 215 |     |     |     |     | 220 |     |     |     |     | 225 |     |     |     |      |
| ATC | AAT | GAG | TTG | TTG | GAC | GCC | ATC | ACT | TCT | TTT | ATA | CTT | CCT | 1311 |
| Ile | Asn | Glu | Leu | Leu | Asp | Ala | Ile | Thr | Ser | Phe | Ile | Leu | Pro |      |
|     | 230 |     |     |     |     | 235 |     |     |     |     | 240 |     |     |      |
| CCG | GCA | TCG | GTC | TCA | AAC | AGA | CTT | TCA | TCT | TAT | CTT | TAT | AAG | 1353 |
| Pro | Ala | Ser | Val | Ser | Asn | Arg | Leu | Ser | Ser | Tyr | Leu | Tyr | Lys |      |
|     |     | 245 |     |     |     |     | 250 |     |     |     |     | 255 |     |      |
| ATA | GAG | CAT | GAC | CCC | AAA | GGA | CAT | AAA | AGA | AGT | TTT | CTA | AAA | 1395 |
| Ile | Glu | His | Asp | Pro | Lys | Gly | His | Lys | Arg | Ser | Phe | Leu | Lys |      |
|     |     |     | 260 |     |     |     |     | 265 |     |     |     |     | 270 |      |
| ATA | ATT | GAC | GGA | AGT | CTG | AGA | CTT | CGA | GAC | GTT | GTA | AGA | ATC | 1437 |
| Ile | Ile | Asp | Gly | Ser | Leu | Arg | Leu | Arg | Asp | Val | Val | Arg | Ile |      |
|     |     |     |     | 275 |     |     |     |     | 280 |     |     |     |     |      |
| AAC | GAT | TCG | GAA | AAA | TTC | ATC | AAG | ATT | AAA | AAT | CTA | AAA | ACT | 1479 |
| Asn | Asp | Ser | Glu | Lys | Phe | Ile | Lys | Ile | Lys | Asn | Leu | Lys | Thr |      |
| 285 |     |     |     |     | 290 |     |     |     |     | 295 |     |     |     |      |
| ATC | AAT | CAG | GGC | AGA | GAG | ATA | AAT | GTT | GAT | GAA | GTG | GGC | GCC | 1521 |
| Ile | Asn | Gln | Gly | Arg | Glu | Ile | Asn | Val | Asp | Glu | Val | Gly | Ala |      |
|     |     | 300 |     |     |     |     | 305 |     |     |     |     | 310 |     |      |
| AAT | GAT | ATC | GCG | ATT | GTA | GAG | GAT | ATG | GAT | GAT | TTT | CGA | ATC | 1563 |
| Asn | Asp | Ile | Ala | Ile | Val | Glu | Asp | Met | Asp | Asp | Phe | Arg | Ile |      |
|     |     |     | 315 |     |     |     |     | 320 |     |     |     |     | 325 |      |
| GGA | AAT | TAT | TTA | GGT | GCT | GAA | CCT | TGT | TTG | ATT | CAA | GGA | TTA | 1605 |
| Gly | Asn | Tyr | Leu | Gly | Ala | Glu | Pro | Cys | Leu | Ile | Gln | Gly | Leu |      |
|     |     |     | 330 |     |     |     |     | 335 |     |     |     |     | 340 |      |
| TCG | CAT | CAG | CAT | CCC | GCT | CTC | AAA | TCC | TCC | GTC | CGG | CCA | GAC | 1647 |
| Ser | His | Gln | His | Pro | Ala | Leu | Lys | Ser | Ser | Val | Arg | Pro | Asp |      |
|     |     |     |     | 345 |     |     |     |     | 350 |     |     |     |     |      |
| AGG | CCC | GAA | GAG | AGA | AGC | AAG | GTG | ATA | TCC | GCT | CTG | AAT | ACA | 1689 |
| Arg | Pro | Glu | Glu | Arg | Ser | Lys | Val | Ile | Ser | Ala | Leu | Asn | Thr |      |
| 355 |     |     |     |     | 360 |     |     |     |     | 365 |     |     |     |      |
| TTG | TGG | ATT | GAA | GAC | CCG | TCT | TTG | TCC | TTT | TCC | ATA | AAC | TCA | 1731 |
| Leu | Trp | Ile | Glu | Asp | Pro | Ser | Leu | Ser | Phe | Ser | Ile | Asn | Ser |      |
|     | 370 |     |     |     |     | 375 |     |     |     |     | 380 |     |     |      |
| TAT | AGT | GAT | GAA | TTG | GAA | ATC | TCG | TTA | TAT | GGT | TTA | ACC | CAA | 1773 |
| Tyr | Ser | Asp | Glu | Leu | Glu | Ile | Ser | Leu | Tyr | Gly | Leu | Thr | Gln |      |
|     |     | 385 |     |     |     |     | 390 |     |     |     |     | 395 |     |      |
| AAG | GAA | ATC | ATA | CAG | ACA | TTG | CTG | GAA | GAA | CGA | TTT | TCC | GTA | 1815 |
| Lys | Glu | Ile | Ile | Gln | Thr | Leu | Leu | Glu | Glu | Arg | Phe | Ser | Val |      |
|     |     |     | 400 |     |     |     |     | 405 |     |     |     |     | 410 |      |
| AAG | GTC | CAT | TTT | GAT | GAG | ATC | AAG | ACT | ATA | TAC | AAA | GAA | GGA | 1857 |
| Lys | Val | His | Phe | Asp | Glu | Ile | Lys | Thr | Ile | Tyr | Lys | Glu | Arg |      |
|     |     |     |     | 415 |     |     |     |     | 420 |     |     |     |     |      |
| CCT | GTA | AAA | AAG | GTC | AAT | AAG | ATT | TAA | CAG | ATC | GAA | GTG | CCG | 1899 |
| Pro | Val | Lys | Lys | Val | Asn | Lys | Ile | Ile | Gln | Ile | Glu | Val | Pro |      |
| 425 |     |     |     |     | 430 |     |     |     |     | 435 |     |     |     |      |
| CCC | AAC | CCT | TAT | TGG | GCC | ACA | ATA | GGG | CTG | ACT | CTT | GAT | CCC | 1941 |
| Pro | Asn | Pro | Tyr | Trp | Ala | Thr | Ile | Gly | Leu | Thr | Leu | Glu | Pro |      |
|     | 440 |     |     |     |     | 445 |     |     |     |     | 450 |     |     |      |

5,322,784

-continued

| | | | | | | | | | | | | | | |
|---|---|---|---|---|---|---|---|---|---|---|---|---|---|---|
| TTA | CCG | TTA | GGG | ACA | GGG | TTG | CAA | ATC | GAA | AGT | GAC | ATC | TCC | 1983 |
| Leu | Pro | Leu | Gly | Thr | Gly | Leu | Gln | Ile | Glu | Ser | Asp | Ile | Ser | |
| | | 455 | | | | 460 | | | | | | 465 | | |
| TAT | GGT | TAT | CTG | AAC | CAT | TCT | TTT | CAA | AAT | GCC | GTT | TTT | GAA | 2025 |
| Tyr | Gly | Tyr | Leu | Asn | His | Ser | Phe | Gln | Asn | Ala | Val | Phe | Glu | |
| | | | 470 | | | | 475 | | | | | | 480 | |
| GGG | ATT | CGT | ATG | TCT | TGC | CAA | TCC | GGG | TTA | CAT | GGA | TGG | GAA | 2067 |
| Gly | Ile | Arg | Met | Ser | Cys | Gln | Ser | Gly | Leu | His | Gly | Trp | Glu | |
| | | | | 485 | | | | | 490 | | | | | |
| GTG | ACT | GAT | CTG | AAA | GTA | ACT | TTT | ACT | CAA | GCC | GAG | TAT | TAT | 2109 |
| Val | Thr | Asp | Leu | Lys | Val | Thr | Phe | Thr | Gln | Ala | Glu | Tyr | Tyr | |
| 495 | | | | | 500 | | | | | 505 | | | | |
| AGC | CCG | GTA | AGT | ACA | CCT | GCT | GAT | TTC | AGA | CAG | CTG | ACC | CCT | 2151 |
| Ser | Pro | Val | Ser | Tyr | Pro | Ala | Asp | Phe | Arg | Gln | Leu | Thr | Pro | |
| | 510 | | | | | 515 | | | | | 520 | | | |
| TAT | GTC | TTC | AGG | CTG | GCC | TTG | CAA | CAG | TCA | GGT | GTG | GAC | ATT | 2193 |
| Tyr | Val | Phe | Arg | Leu | Ala | Leu | Gln | Gln | Ser | Gly | Val | Asp | Ile | |
| | | 525 | | | | | 530 | | | | | 535 | | |
| CTC | GAA | CCG | ATG | CTC | TAT | TTT | GAG | TTG | CAG | ATA | CCC | CAA | GCG | 2235 |
| Leu | Glu | Pro | Met | Leu | Tyr | Phe | Glu | Leu | Gln | Ile | Pro | Gln | Ala | |
| | | | 540 | | | | 545 | | | | | | 550 | |
| GCA | AGT | TCC | AAA | GCT | ATT | ACA | GAT | TTG | CAA | AAA | ATG | ATG | TCT | 2277 |
| Ala | Ser | Ser | Lys | Ala | Ile | Thr | Asp | Leu | Gln | Lys | Met | Met | Ser | |
| | | | | 555 | | | | | 560 | | | | | |
| GAG | ATT | GAA | GAC | ATC | AGT | TGC | AAT | AAT | GAG | TGG | TGT | CAT | ATT | 2319 |
| Glu | Ile | Glu | Asp | Ile | Ser | Cys | Asn | Asn | Glu | Trp | Cys | His | Ile | |
| 565 | | | | | 570 | | | | | 575 | | | | |
| AAA | GGG | AAA | GTT | CCA | TTA | AAT | ACA | AGT | AAA | GAC | TAT | GCA | TCA | 2361 |
| Lys | Gly | Lys | Val | Pro | Leu | Asn | Thr | Ser | Lys | Asp | Tyr | Ala | Ser | |
| | 580 | | | | | 585 | | | | | 590 | | | |
| GAA | GTA | AGT | TCA | TAC | ACT | AAG | GGC | TTA | GGC | ATT | TTT | ATG | GTT | 2403 |
| Glu | Val | Ser | Ser | Tyr | Thr | Lys | Gly | Leu | Gly | Ile | Phe | Met | Val | |
| | | 595 | | | | | 600 | | | | | 605 | | |
| AAG | CCA | TGC | GGG | TAT | CAA | ATA | ACA | AAA | GGC | GGT | TAT | TCT | GAT | 2445 |
| Lys | Pro | Cys | Gly | Tyr | Gln | Ile | Thr | Lys | Gly | Gly | Tyr | Ser | Asp | |
| | | | 610 | | | | | 615 | | | | | 620 | |
| AAT | ATC | CGC | ATG | AAC | GAA | AAA | GAT | AAA | CTT | TTA | TTC | ATG | TTC | 2487 |
| Asn | Ile | Arg | Met | Asn | Glu | Lys | Asp | Lys | Leu | Leu | Phe | Met | Phe | |
| | | | | 625 | | | | | 630 | | | | | |
| CAA | AAA | TCA | ATG | TCA | TCA | AAA | TAATGGAGCG | GTCAGGAAAT | | | | | | 2528 |
| Gln | Lys | Ser | Met | Ser | Ser | Lys | | | | | | | | |
| 635 | | | | | 640 | | | | | | | | | |

TTCTATAAGG CAATACAGTT GGGATATATA CTTATCTCCA TTCTTATCGG 2578

ATGTATGGCA TATAATAGCC TCTATGAATG GCAGGAGATA GAAGCATTAG 2628

AACTTGGCAA TAAAAAATA GACGAGCTC 2657

( 2 ) INFORMATION FOR SEQ ID NO:3:

( i ) SEQUENCE CHARACTERISTICS:
        ( A ) LENGTH: 641 amino acids
        ( B ) TYPE: amino acid
        ( C ) STRANDEDNESS:
        ( D ) TOPOLOGY: unknown ( x i ) SEQUENCE DESCRIPTION: SEQ ID NO:3:

| | | | | | | | | | | | | | | |
|---|---|---|---|---|---|---|---|---|---|---|---|---|---|---|
| Met | Asn | Ile | Ile | Asn | Leu | Gly | Ile | Leu | Ala | His | Ile | Asp | Ala | Gly |
| | | | | 5 | | | | | 10 | | | | | 15 |
| Lys | Thr | Ser | Val | Thr | Glu | Asn | Leu | Leu | Phe | Ala | Ser | Gly | Ala | Thr |
| | | | | 20 | | | | | 25 | | | | | 30 |
| Glu | Lys | Cys | Gly | Cys | Val | Asp | Asn | Gly | Asp | Thr | Ile | Thr | Asp | Ser |
| | | | | 35 | | | | | 40 | | | | | 45 |

-continued

| | | | | | | | | | | | | | |
|---|---|---|---|---|---|---|---|---|---|---|---|---|---|
| Met | Asp | Ile | Glu | Lys<br>50 | Arg | Arg | Gly | Ile | Thr<br>55 | Val | Arg | Ala | Ser | Thr<br>60 |
| Thr | Ser | Ile | Ile | Trp<br>65 | Asn | Gly | Val | Lys | Cys<br>70 | Asn | Ile | Ile | Asp | Thr<br>75 |
| Pro | Gly | His | Met | Asp<br>80 | Phe | Ile | Ala | Glu | Val<br>85 | Glu | Arg | Thr | Phe | Lys<br>90 |
| Met | Leu | Asp | Gly | Ala<br>95 | Val | Leu | Ile | Leu | Ser<br>100 | Ala | Lys | Glu | Gly | Ile<br>105 |
| Gln | Ala | Gln | Thr | Lys<br>110 | Leu | Leu | Phe | Asn | Thr<br>115 | Leu | Gln | Lys | Leu | Gln<br>120 |
| Ile | Pro | Thr | Ile | Ile<br>125 | Phe | Ile | Asn | Lys | Ile<br>130 | Asp | Arg | Ala | Gly | Val<br>135 |
| Asn | Leu | Glu | Arg | Leu<br>140 | Tyr | Leu | Asp | Ile | Lys<br>145 | Ala | Asn | Leu | Ser | Gln<br>150 |
| Asp | Val | Leu | Phe | Met<br>155 | Gln | Asn | Val | Val | Asp<br>160 | Gly | Ser | Val | Tyr | Pro<br>165 |
| Val | Cys | Ser | Gln | Thr<br>170 | Tyr | Ile | Lys | Glu | Glu<br>175 | Tyr | Lys | Glu | Phe | Val<br>180 |
| Cys | Asn | His | Asp | Asp<br>185 | Asn | Ile | Leu | Glu | Arg<br>190 | Tyr | Leu | Ala | Asp | Ser<br>195 |
| Glu | Ile | Ser | Pro | Ala<br>200 | Asp | Tyr | Trp | Asn | Thr<br>205 | Ile | Ile | Ala | Leu | Val<br>210 |
| Ala | Lys | Ala | Lys | Val<br>215 | Tyr | Pro | Val | Leu | His<br>220 | Gly | Ser | Ala | Met | Phe<br>225 |
| Asn | Ile | Gly | Ile | Asn<br>230 | Glu | Leu | Leu | Asp | Ala<br>235 | Ile | Thr | Ser | Phe | Ile<br>240 |
| Leu | Pro | Pro | Ala | Ser<br>245 | Val | Ser | Asn | Arg | Leu<br>250 | Ser | Ser | Tyr | Leu | Tyr<br>255 |
| Lys | Ile | Glu | His | Asp<br>260 | Pro | Lys | Gly | His | Lys<br>265 | Arg | Ser | Phe | Leu | Lys<br>270 |
| Ile | Ile | Asp | Gly | Ser<br>275 | Leu | Arg | Leu | Arg | Asp<br>280 | Val | Val | Arg | Ile | Asn<br>285 |
| Asp | Ser | Glu | Lys | Phe<br>290 | Ile | Lys | Ile | Lys | Asn<br>295 | Leu | Lys | Thr | Ile | Asn<br>300 |
| Gln | Gly | Arg | Glu | Ile<br>305 | Asn | Val | Asp | Glu | Val<br>310 | Gly | Ala | Asn | Asp | Ile<br>315 |
| Ala | Ile | Val | Glu | Asp<br>320 | Met | Asp | Asp | Phe | Arg<br>325 | Ile | Gly | Asn | Tyr | Leu<br>330 |
| Gly | Ala | Glu | Pro | Cys<br>335 | Leu | Ile | Gln | Gly | Leu<br>340 | Ser | His | Gln | His | Pro<br>345 |
| Ala | Leu | Lys | Ser | Ser<br>350 | Val | Arg | Pro | Asp | Arg<br>355 | Pro | Glu | Glu | Arg | Ser<br>360 |
| Lys | Val | Ile | Ser | Ala<br>365 | Leu | Asn | Thr | Leu | Trp<br>370 | Ile | Glu | Asp | Pro | Ser<br>375 |
| Leu | Ser | Phe | Ser | Ile<br>380 | Asn | Ser | Tyr | Ser | Asp<br>385 | Glu | Leu | Glu | Ile | Ser<br>390 |
| Leu | Tyr | Gly | Leu | Thr<br>395 | Gln | Lys | Glu | Ile | Ile<br>400 | Gln | Thr | Leu | Leu | Glu<br>405 |
| Glu | Arg | Phe | Ser | Val<br>410 | Lys | Val | His | Phe | Asp<br>415 | Glu | Ile | Lys | Thr | Ile<br>420 |
| Tyr | Lys | Glu | Arg | Pro<br>425 | Val | Lys | Lys | Val | Asn<br>430 | Lys | Ile | Ile | Gln | Ile<br>435 |
| Glu | Val | Pro | Pro | Asn<br>440 | Pro | Tyr | Trp | Ala | Thr<br>445 | Ile | Gly | Leu | Thr | Leu<br>450 |
| Glu | Pro | Leu | Pro | Leu | Gly | Thr | Gly | Leu | Gln | Ile | Glu | Ser | Asp | Ile |

|  |  | 455 |  |  |  |  | 460 |  |  |  |  | 465 |
|---|---|---|---|---|---|---|---|---|---|---|---|---|

Ser Tyr Gly Tyr Leu Asn His Ser Phe Gln Asn Ala Val Phe Glu
            470                     475                 480

Gly Ile Arg Met Ser Cys Gln Ser Gly Leu His Gly Trp Glu Val
            485                     490                 495

Thr Asp Leu Lys Val Thr Phe Thr Gln Ala Glu Tyr Tyr Ser Pro
            500                     505                 510

Val Ser Tyr Pro Ala Asp Phe Arg Gln Leu Thr Pro Tyr Val Phe
            515                     520                 525

Arg Leu Ala Leu Gln Gln Ser Gly Val Asp Ile Leu Glu Pro Met
            530                     535                 540

Leu Tyr Phe Glu Leu Gln Ile Pro Gln Ala Ala Ser Ser Lys Ala
            545                     550                 555

Ile Thr Asp Leu Gln Lys Met Met Ser Glu Ile Glu Asp Ile Ser
            560                     565                 570

Cys Asn Asn Glu Trp Cys His Ile Lys Gly Lys Val Pro Leu Asn
            575                     580                 585

Thr Ser Lys Asp Tyr Ala Ser Glu Val Ser Ser Tyr Thr Lys Gly
            590                     595                 600

Leu Gly Ile Phe Met Val Lys Pro Cys Gly Tyr Gln Ile Thr Lys
            605                     610                 615

Gly Gly Tyr Ser Asp Asn Ile Arg Met Asn Glu Lys Asp Lys Leu
            620                     625                 630

Leu Phe Met Phe Gln Lys Ser Met Ser Ser Lys
            635                     640

(2) INFORMATION FOR SEQ ID NO:4:

(i) SEQUENCE CHARACTERISTICS:
        (A) LENGTH: 2106 base pairs
        (B) TYPE: nucleic acid
        (C) STRANDEDNESS: double stranded
        (D) TOPOLOGY: circular (xi) SEQUENCE DESCRIPTION: SEQ ID NO:4:

```
AAAAATCCTC CTACTTTTGT TAGATATATT TTTTTGTGTA ATTTTGTAAT        50

CGTTATGCGG CAGTAATAAT ATACATATTA ATACGAGTTA GGAATCCTGT       100

AGTTCTCATA TGCTACGAGG AGGTATTAAA AGGTGCGTTT CGACAATGCA       150

TCTATTGTAG TATATTATTG CTTAATCCAA ATG AAT ATT ATA             192
                                  Met Asn Ile Ile
AAT TTA GGA ATT CTT GCT CAC ATT GAT GCA GGA AAA ACT TCC      234
Asn Leu Gly Ile Leu Ala His Ile Asp Ala Gly Lys Thr Ser
 5              10                  15

GTA ACC GAG AAT CTG CTG TTT GCC AGT GGA GCA ACG GAA AAG      276
Val Thr Glu Asn Leu Leu Phe Ala Ser Gly Ala Thr Glu Lys
    20              25                  30

TGC GGC TGT GTG GAT AAT GGT GAC ACC ATA ACG GAC TCT ATG      318
Cys Gly Cys Val Asp Asn Gly Asp Thr Ile Thr Asp Ser Met
        35                  40                  45

GAT ATA GAG AAA CGT AGA GGA ATT ACT GTT CGG GCT TCT ACG      360
Asp Ile Glu Lys Arg Arg Gly Ile Thr Val Arg Ala Ser Thr
            50                  55                  60

ACA TCT ATT ATC TGG AAT GGT GTG AAA TGC AAT ATC ATT GAC      402
Thr Ser Ile Ile Trp Asn Gly Val Lys Cys Asn Ile Ile Asp
                65                  70

ACT CCG GGA CAC ATG GAT TTT ATT GCG GAA GTG GAG CGG ACA      444
Thr Pro Gly His Met Asp Phe Ile Ala Glu Val Glu Arg Thr
 75                  80                  85
```

| | |
|---|---|
| TTC AAA ATG CTT GAT GGA GCA GTC CTC ATC TTA TCC GCA AAG<br>Phe Lys Met Leu Asp Gly Ala Val Leu Ile Leu Ser Ala Lys<br>90                           95                         100 | 486 |
| GAA GGC ATA CAA GCG CAG ACA AAG TTG CTG TTC AAT ACT TTA<br>Glu Gly Ile Gln Ala Gln Thr Lys Leu Leu Phe Asn Thr Leu<br>105                     110                     115 | 528 |
| CAG AAG CTG CAA ATC CCG ACA ATT ATA TTT ATC AAT AAG ATT<br>Gln Lys Leu Gln Ile Pro Thr Ile Ile Phe Ile Asn Lys Ile<br>            120                     125                   130 | 570 |
| GAC CGA GCC GGT GTG AAT TTG GAG CGT TTG TAT CTG GAT ATA<br>Asp Arg Ala Gly Val Asn Leu Glu Arg Leu Tyr Leu Asp Ile<br>                  135                        140 | 612 |
| AAA GCA AAT CTG TCT CAA GAT GTC CTG TTT ATG CAA AAT GTT<br>Lys Ala Asn Leu Ser Gln Asp Val Leu Phe Met Gln Asn Val<br>145                     150                     155 | 654 |
| GTC GAT GGA TCG GTT TAT CCG GTT TGC TCC CAA ACA TAT ATA<br>Val Asp Gly Ser Val Tyr Pro Val Cys Ser Gln Thr Tyr Ile<br>      160                     165                     170 | 696 |
| AAG GAA GAA TAC AAA GAA TTT GTA TGC AAC CAT GAC GAC AAT<br>Lys Glu Glu Tyr Lys Glu Phe Val Cys Asn His Asp Asp Asn<br>               175                    180                185 | 738 |
| ATA TTA GAA CGA TAT TTG GCG GAT AGC GAA ATT TCA CCG GCT<br>Ile Leu Glu Arg Tyr Leu Ala Asp Ser Glu Ile Ser Pro Ala<br>                  190                    195               200 | 780 |
| GAT TAT TGG AAT ACG ATA ATC GCT CTT GTG GCA AAA GCC AAA<br>Asp Tyr Trp Asn Thr Ile Ile Ala Leu Val Ala Lys Ala Lys<br>                     205                     210 | 822 |
| GTC TAT CCG GTG CTA CAT GGA TCA GCA ATG TTC AAT ATC GGT<br>Val Tyr Pro Val Leu His Gly Ser Ala Met Phe Asn Ile Gly<br>215                     220                     225 | 864 |
| ATC AAT GAG TTG TTG GAC GCC ATC ACT TCT TTT ATA CTT CCT<br>Ile Asn Glu Leu Leu Asp Ala Ile Thr Ser Phe Ile Leu Pro<br>      230                     235                     240 | 906 |
| CCG GCA TCG GTC TCA AAC AGA CTT TCA TCT TAT CTT TAT AAG<br>Pro Ala Ser Val Ser Asn Arg Leu Ser Ser Tyr Leu Tyr Lys<br>               245                    250                255 | 948 |
| ATA GAG CAT GAC CCC AAA GGA CAT AAA AGA AGT TTT CTA AAA<br>Ile Glu His Asp Pro Lys Gly His Lys Arg Ser Phe Leu Lys<br>                  260                    265               270 | 990 |
| ATA ATT GAC GGA AGT CTG AGA CTT CGA GAC GTT GTA AGA ATC<br>Ile Ile Asp Gly Ser Leu Arg Leu Arg Asp Val Val Arg Ile<br>                     275                     280 | 1032 |
| AAC GAT TCG GAA AAA TTC ATC AAG ATT AAA AAT CTA AAA ACT<br>Asn Asp Ser Glu Lys Phe Ile Lys Ile Lys Asn Leu Lys Thr<br>285                     290                     295 | 1074 |
| ATC AAT CAG GGC AGA GAG ATA AAT GTT GAT GAA GTG GGC GCC<br>Ile Asn Gln Gly Arg Glu Ile Asn Val Asp Glu Val Gly Ala<br>      300                     305                     310 | 1116 |
| AAT GAT ATC GCG ATT GTA GAG GAT ATG GAT GAT TTT CGA ATC<br>Asn Asp Ile Ala Ile Val Glu Asp Met Asp Asp Phe Arg Ile<br>               315                    320                325 | 1158 |
| GGA AAT TAT TTA GGT GCT GAA CCT TGT TTG ATT CAA GGA TTA<br>Gly Asn Tyr Leu Gly Ala Glu Pro Cys Leu Ile Gln Gly Leu<br>                  330                    335               340 | 1200 |
| TCG CAT CAG CAT CCC GCT CTC AAA TCC TCC GTC CGG CCA GAC<br>Ser His Gln His Pro Ala Leu Lys Ser Ser Val Arg Pro Asp<br>                     345                    350 | 1242 |
| AGG CCC GAA GAG AGA AGC AAG GTG ATA TCC GCT CTG AAT ACA<br>Arg Pro Glu Glu Arg Ser Lys Val Ile Ser Ala Leu Asn Thr<br>355                     360                    365 | 1284 |
| TTG TGG ATT GAA GAC CCG TCT TTG TCC TTT TCC ATA AAC TCA<br>Leu Trp Ile Glu Asp Pro Ser Leu Ser Phe Ser Ile Asn Ser | 1326 |

|  |  |  |  |  |  |  |  |  |  |  |  |  |  |
|---|---|---|---|---|---|---|---|---|---|---|---|---|---|
| | 370 | | | | 375 | | | | | 380 | | | |
| TAT | AGT | GAT | GAA | TTG | GAA | ATC | TCG | TTA | TAT | GGT | TTA | ACC | CAA | 1368 |
| Tyr | Ser | Asp 385 | Glu | Leu | Glu | Ile | Ser 390 | Leu | Tyr | Gly | Leu | Thr 395 | Gln |
| AAG | GAA | ATC | ATA | CAG | ACA | TTG | CTG | GAA | GAA | CGA | TTT | TCC | GTA | 1410 |
| Lys | Glu | Ile | Ile 400 | Gln | Thr | Leu | Leu | Glu 405 | Glu | Arg | Phe | Ser | Val 410 |
| AAG | GTC | CAT | TTT | GAT | GAG | ATC | AAG | ACT | ATA | TAC | AAA | GAA | GGA | 1452 |
| Lys | Val | His | Phe | Asp 415 | Glu | Ile | Lys | Thr | Ile 420 | Tyr | Lys | Glu | Arg |
| CCT | GTA | AAA | AAG | GTC | AAT | AAG | ATT | TAA | CAG | ATC | GAA | GTG | CCG | 1494 |
| Pro 425 | Val | Lys | Lys | Val | Asn 430 | Lys | Ile | Ile | Gln | Ile 435 | Glu | Val | Pro |
| CCC | AAC | CCT | TAT | TGG | GCC | ACA | ATA | GGG | CTG | ACT | CTT | GAT | CCC | 1536 |
| Pro | Asn 440 | Pro | Tyr | Trp | Ala | Thr | Ile 445 | Gly | Leu | Thr | Leu | Glu 450 | Pro |
| TTA | CCG | TTA | GGG | ACA | GGG | TTG | CAA | ATC | GAA | AGT | GAC | ATC | TCC | 1578 |
| Leu | Pro | Leu 455 | Gly | Thr | Gly | Leu | Gln 460 | Ile | Glu | Ser | Asp | Ile 465 | Ser |
| TAT | GGT | TAT | CTG | AAC | CAT | TCT | TTT | CAA | AAT | GCC | GTT | TTT | GAA | 1620 |
| Tyr | Gly | Tyr | Leu 470 | Asn | His | Ser | Phe | Gln 475 | Asn | Ala | Val | Phe | Glu 480 |
| GGG | ATT | CGT | ATG | TCT | TGC | CAA | TCC | GGG | TTA | CAT | GGA | TGG | GAA | 1662 |
| Gly | Ile | Arg | Met | Ser 485 | Cys | Gln | Ser | Gly | Leu 490 | His | Gly | Trp | Glu |
| GTG | ACT | GAT | CTG | AAA | GTA | ACT | TTT | ACT | CAA | GCC | GAG | TAT | TAT | 1704 |
| Val | Thr | Asp 495 | Leu | Lys | Val | Thr 500 | Phe | Thr | Gln | Ala 505 | Glu | Tyr | Tyr |
| AGC | CCG | GTA | AGT | ACA | CCT | GCT | GAT | TTC | AGA | CAG | CTG | ACC | CCT | 1746 |
| Ser | Pro | Val 510 | Ser | Tyr | Pro | Ala | Asp 515 | Phe | Arg | Gln | Leu | Thr 520 | Pro |
| TAT | GTC | TTC | AGG | CTG | GCC | TTG | CAA | CAG | TCA | GGT | GTG | GAC | ATT | 1788 |
| Tyr | Val | Phe 525 | Arg | Leu | Ala | Leu | Gln 530 | Gln | Ser | Gly | Val | Asp 535 | Ile |
| CTC | GAA | CCG | ATG | CTC | TAT | TTT | GAG | TTG | CAG | ATA | CCC | CAA | GCG | 1830 |
| Leu | Glu | Pro | Met 540 | Leu | Tyr | Phe | Glu | Leu 545 | Gln | Ile | Pro | Gln | Ala 550 |
| GCA | AGT | TCC | AAA | GCT | ATT | ACA | GAT | TTG | CAA | AAA | ATG | ATG | TCT | 1872 |
| Ala | Ser | Ser | Lys | Ala 555 | Ile | Thr | Asp | Leu | Gln 560 | Lys | Met | Met | Ser |
| GAG | ATT | GAA | GAC | ATC | AGT | TGC | AAT | AAT | GAG | TGG | TGT | CAT | ATT | 1914 |
| Glu 565 | Ile | Glu | Asp | Ile | Ser 570 | Cys | Asn | Asn | Glu | Trp 575 | Cys | His | Ile |
| AAA | GGG | AAA | GTT | CCA | TTA | AAT | ACA | AGT | AAA | GAC | TAT | GCA | TCA | 1956 |
| Lys | Gly 580 | Lys | Val | Pro | Leu | Asn 585 | Thr | Ser | Lys | Asp | Tyr 590 | Ala | Ser |
| GAA | GTA | AGT | TCA | TAC | ACT | AAG | GGC | TTA | GGC | ATT | TTT | ATG | GTT | 1998 |
| Glu | Val | Ser 595 | Ser | Tyr | Thr | Lys | Gly 600 | Leu | Gly | Ile | Phe | Met 605 | Val |
| AAG | CCA | TGC | GGG | TAT | CAA | ATA | ACA | AAA | GGC | GGT | TAT | TCT | GAT | 2040 |
| Lys | Pro | Cys | Gly 610 | Tyr | Gln | Ile | Thr | Lys 615 | Gly | Gly | Tyr | Ser | Asp 620 |
| AAT | ATC | CGC | ATG | AAC | GAA | AAA | GAT | AAA | CTT | TTA | TTC | ATG | TTC | 2082 |
| Asn | Ile | Arg | Met | Asn 625 | Glu | Lys | Asp | Lys | Leu 630 | Leu | Phe | Met | Phe |
| CAA | AAA | TCA | ATG | TCA | TCA | AAA | TAA | | | | | | | 2106 |
| Gln | Lys | Ser | Met | Ser 640 | Ser | Lys | | | | | | | |
| Gln 635 | | | | | | | | | | | | | |

( 2 ) INFORMATION FOR SEQ ID NO:5:

( i ) SEQUENCE CHARACTERISTICS:

(A) LENGTH: 1926 base pairs
(B) TYPE: nucleic acid
(C) STRANDEDNESS: double stranded
(D) TOPOLOGY: circular (xi) SEQUENCE DESCRIPTION: SEQ ID NO:5:

```
ATG AAT ATT ATA AAT TTA GGA ATT CTT GCT CAC ATT GAT GCA      42
Met Asn Ile Ile Asn Leu Gly Ile Leu Ala His Ile Asp Ala
             5                  10

GGA AAA ACT TCC GTA ACC GAG AAT CTG CTG TTT GCC AGT GGA      84
Gly Lys Thr Ser Val Thr Glu Asn Leu Leu Phe Ala Ser Gly
 15              20                  25

GCA ACG GAA AAG TGC GGC TGT GTG GAT AAT GGT GAC ACC ATA     126
Ala Thr Glu Lys Cys Gly Cys Val Asp Asn Gly Asp Thr Ile
     30              35              40

ACG GAC TCT ATG GAT ATA GAG AAA CGT AGA GGA ATT ACT GTT     168
Thr Asp Ser Met Asp Ile Glu Lys Arg Arg Gly Ile Thr Val
         45              50              55

CGG GCT TCT ACG ACA TCT ATT ATC TGG AAT GGT GTG AAA TGC     210
Arg Ala Ser Thr Thr Ser Ile Ile Trp Asn Gly Val Lys Cys
             60              65              70

AAT ATC ATT GAC ACT CCG GGA CAC ATG GAT TTT ATT GCG GAA     252
Asn Ile Ile Asp Thr Pro Gly His Met Asp Phe Ile Ala Glu
                 75              80

GTG GAG CGG ACA TTC AAA ATG CTT GAT GGA GCA GTC CTC ATC     294
Val Glu Arg Thr Phe Lys Met Leu Asp Gly Ala Val Leu Ile
 85              90              95

TTA TCC GCA AAG GAA GGC ATA CAA GCG CAG ACA AAG TTG CTG     336
Leu Ser Ala Lys Glu Gly Ile Gln Ala Gln Thr Lys Leu Leu
 100             105             110

TTC AAT ACT TTA CAG AAG CTG CAA ATC CCG ACA ATT ATA TTT     378
Phe Asn Thr Leu Gln Lys Leu Gln Ile Pro Thr Ile Ile Phe
     115             120             125

ATC AAT AAG ATT GAC CGA GCC GGT GTG AAT TTG GAG CGT TTG     420
Ile Asn Lys Ile Asp Arg Ala Gly Val Asn Leu Glu Arg Leu
         130             135             140

TAT CTG GAT ATA AAA GCA AAT CTG TCT CAA GAT GTC CTG TTT     462
Tyr Leu Asp Ile Lys Ala Asn Leu Ser Gln Asp Val Leu Phe
             145             150

ATG CAA AAT GTT GTC GAT GGA TCG GTT TAT CCG GTT TGC TCC     504
Met Gln Asn Val Val Asp Gly Ser Val Tyr Pro Val Cys Ser
155             160             165

CAA ACA TAT ATA AAG GAA GAA TAC AAA GAA TTT GTA TGC AAC     546
Gln Thr Tyr Ile Lys Glu Glu Tyr Lys Glu Phe Val Cys Asn
     170             175             180

CAT GAC GAC AAT ATA TTA GAA CGA TAT TTG GCG GAT AGC GAA     588
His Asp Asp Asn Ile Leu Glu Arg Tyr Leu Ala Asp Ser Glu
         185             190             195

ATT TCA CCG GCT GAT TAT TGG AAT ACG ATA ATC GCT CTT GTG     630
Ile Ser Pro Ala Asp Tyr Trp Asn Thr Ile Ile Ala Leu Val
             200             205             210

GCA AAA GCC AAA GTC TAT CCG GTG CTA CAT GGA TCA GCA ATG     672
Ala Lys Ala Lys Val Tyr Pro Val Leu His Gly Ser Ala Met
             215             220

TTC AAT ATC GGT ATC AAT GAG TTG TTG GAC GCC ATC ACT TCT     714
Phe Asn Ile Gly Ile Asn Glu Leu Leu Asp Ala Ile Thr Ser
225             230             235

TTT ATA CTT CCT CCG GCA TCG GTC TCA AAC AGA CTT TCA TCT     756
Phe Ile Leu Pro Pro Ala Ser Val Ser Asn Arg Leu Ser Ser
     240             245             250

TAT CTT TAT AAG ATA GAG CAT GAC CCC AAA GGA CAT AAA AGA     798
Tyr Leu Tyr Lys Ile Glu His Asp Pro Lys Gly His Lys Arg
         255             260             265
```

|     |     |     |     |     |     |     |     |     |     |     |     |     |     |      |
|-----|-----|-----|-----|-----|-----|-----|-----|-----|-----|-----|-----|-----|-----|------|
| AGT | TTT | CTA | AAA | ATA | ATT | GAC | GGA | AGT | CTG | AGA | CTT | CGA | GAC | 840  |
| Ser | Phe | Leu | Lys | Ile | Ile | Asp | Gly | Ser | Leu | Arg | Leu | Arg | Asp |      |
|     |     |     | 270 |     |     |     |     | 275 |     |     |     |     | 280 |      |
| GTT | GTA | AGA | ATC | AAC | GAT | TCG | GAA | AAA | TTC | ATC | AAG | ATT | AAA | 882  |
| Val | Val | Arg | Ile | Asn | Asp | Ser | Glu | Lys | Phe | Ile | Lys | Ile | Lys |      |
|     |     |     |     | 285 |     |     |     |     | 290 |     |     |     |     |      |
| AAT | CTA | AAA | ACT | ATC | AAT | CAG | GGC | AGA | GAG | ATA | AAT | GTT | GAT | 924  |
| Asn | Leu | Lys | Thr | Ile | Asn | Gln | Gly | Arg | Glu | Ile | Asn | Val | Asp |      |
| 295 |     |     |     |     | 300 |     |     |     |     | 305 |     |     |     |      |
| GAA | GTG | GGC | GCC | AAT | GAT | ATC | GCG | ATT | GTA | GAG | GAT | ATG | GAT | 966  |
| Glu | Val | Gly | Ala | Asn | Asp | Ile | Ala | Ile | Val | Glu | Asp | Met | Asp |      |
|     |     | 310 |     |     |     |     | 315 |     |     |     | 320 |     |     |      |
| GAT | TTT | CGA | ATC | GGA | AAT | TAT | TTA | GGT | GCT | GAA | CCT | TGT | TTG | 1008 |
| Asp | Phe | Arg | Ile | Gly | Asn | Tyr | Leu | Gly | Ala | Glu | Pro | Cys | Leu |      |
|     |     | 325 |     |     |     |     | 330 |     |     |     | 335 |     |     |      |
| ATT | CAA | GGA | TTA | TCG | CAT | CAG | CAT | CCC | GCT | CTC | AAA | TCC | TCC | 1050 |
| Ile | Gln | Gly | Leu | Ser | His | Gln | His | Pro | Ala | Leu | Lys | Ser | Ser |      |
|     |     |     | 340 |     |     |     |     | 345 |     |     |     |     | 350 |      |
| GTC | CGG | CCA | GAC | AGG | CCC | GAA | GAG | AGA | AGC | AAG | GTG | ATA | TCC | 1092 |
| Val | Arg | Pro | Asp | Arg | Pro | Glu | Glu | Arg | Ser | Lys | Val | Ile | Ser |      |
|     |     |     |     | 355 |     |     |     |     | 360 |     |     |     |     |      |
| GCT | CTG | AAT | ACA | TTG | TGG | ATT | GAA | GAC | CCG | TCT | TTG | TCC | TTT | 1134 |
| Ala | Leu | Asn | Thr | Leu | Trp | Ile | Glu | Asp | Pro | Ser | Leu | Ser | Phe |      |
| 365 |     |     |     |     | 370 |     |     |     |     | 375 |     |     |     |      |
| TCC | ATA | AAC | TCA | TAT | AGT | GAT | GAA | TTG | GAA | ATC | TCG | TTA | TAT | 1176 |
| Ser | Ile | Asn | Ser | Tyr | Ser | Asp | Glu | Leu | Glu | Ile | Ser | Leu | Tyr |      |
|     | 380 |     |     |     |     | 385 |     |     |     |     | 390 |     |     |      |
| GGT | TTA | ACC | CAA | AAG | GAA | ATC | ATA | CAG | ACA | TTG | CTG | GAA | GAA | 1218 |
| Gly | Leu | Thr | Gln | Lys | Glu | Ile | Ile | Gln | Thr | Leu | Leu | Glu | Glu |      |
|     |     | 395 |     |     |     |     | 400 |     |     |     |     | 405 |     |      |
| CGA | TTT | TCC | GTA | AAG | GTC | CAT | TTT | GAT | GAG | ATC | AAG | ACT | ATA | 1260 |
| Arg | Phe | Ser | Val | Lys | Val | His | Phe | Asp | Glu | Ile | Lys | Thr | Ile |      |
|     |     |     | 410 |     |     |     |     | 415 |     |     |     |     | 420 |      |
| TAC | AAA | GAA | GGA | CCT | GTA | AAA | AAG | GTC | AAT | AAG | ATT | TAA | CAG | 1302 |
| Tyr | Lys | Glu | Arg | Pro | Val | Lys | Lys | Val | Asn | Lys | Ile | Ile | Gln |      |
|     |     |     |     | 425 |     |     |     |     | 430 |     |     |     |     |      |
| ATC | GAA | GTG | CCG | CCC | AAC | CCT | TAT | TGG | GCC | ACA | ATA | GGG | CTG | 1344 |
| Ile | Glu | Val | Pro | Pro | Asn | Pro | Tyr | Trp | Ala | Thr | Ile | Gly | Leu |      |
| 435 |     |     |     |     | 440 |     |     |     |     | 445 |     |     |     |      |
| ACT | CTT | GAT | CCC | TTA | CCG | TTA | GGG | ACA | GGG | TTG | CAA | ATC | GAA | 1386 |
| Thr | Leu | Asp | Pro | Leu | Pro | Leu | Gly | Thr | Gly | Leu | Gln | Ile | Glu |      |
|     |     | 450 |     |     |     |     | 455 |     |     |     |     | 460 |     |      |
| AGT | GAC | ATC | TCC | TAT | GGT | TAT | CTG | AAC | CAT | TCT | TTT | CAA | AAT | 1428 |
| Ser | Asp | Ile | Ser | Tyr | Gly | Tyr | Leu | Asn | His | Ser | Phe | Gln | Asn |      |
|     |     |     | 465 |     |     |     |     | 470 |     |     |     |     | 475 |      |
| GCC | GTT | TTT | GAA | GGG | ATT | CGT | ATG | TCT | TGC | CAA | TCC | GGG | TTA | 1470 |
| Ala | Val | Phe | Glu | Gly | Ile | Arg | Met | Ser | Cys | Gln | Ser | Gly | Leu |      |
|     |     |     | 480 |     |     |     |     | 485 |     |     |     |     | 490 |      |
| CAT | GGA | TGG | GAA | GTG | ACT | GAT | CTG | AAA | GTA | ACT | TTT | ACT | CAA | 1512 |
| His | Gly | Trp | Glu | Val | Thr | Asp | Leu | Lys | Val | Thr | Phe | Thr | Gln |      |
|     |     |     |     | 495 |     |     |     |     | 500 |     |     |     |     |      |
| GCC | GAG | TAT | TAT | AGC | CCG | GTA | AGT | ACA | CCT | GCT | GAT | TTC | AGA | 1554 |
| Ala | Glu | Tyr | Tyr | Ser | Pro | Val | Ser | Tyr | Pro | Ala | Asp | Phe | Arg |      |
| 505 |     |     |     |     | 510 |     |     |     |     | 515 |     |     |     |      |
| CAG | CTG | ACC | CCT | TAT | GTC | TTC | AGG | CTG | GCC | TTG | CAA | CAG | TCA | 1596 |
| Gln | Leu | Thr | Pro | Tyr | Val | Phe | Arg | Leu | Ala | Leu | Gln | Gln | Ser |      |
|     |     | 520 |     |     |     |     | 525 |     |     |     |     | 530 |     |      |
| GGT | GTG | GAC | ATT | CTC | GAA | CCG | ATG | CTC | TAT | TTT | GAG | TTG | CAG | 1638 |
| Gly | Val | Asp | Ile | Leu | Glu | Pro | Met | Leu | Tyr | Phe | Glu | Leu | Gln |      |
|     |     | 535 |     |     |     |     | 540 |     |     |     |     | 545 |     |      |
| ATA | CCC | CAA | GCG | GCA | AGT | TCC | AAA | GCT | ATT | ACA | GAT | TTG | CAA | 1680 |

-continued

| | | | | | | | | | | | | |
|---|---|---|---|---|---|---|---|---|---|---|---|---|
| Ile | Pro | Gln | Ala | Ala | Ser | Ser | Lys | Ala | Ile | Thr | Asp | Leu | Gln |
| | | | 550 | | | | | 555 | | | | | 560 |

| AAA | ATG | ATG | TCT | GAG | ATT | GAA | GAC | ATC | AGT | TGC | AAT | AAT | GAG | 1722 |
|---|---|---|---|---|---|---|---|---|---|---|---|---|---|---|
| Lys | Met | Met | Ser | Glu | Ile | Glu | Asp | Ile | Ser | Cys | Asn | Asn | Glu | |
| | | | | 565 | | | | | 570 | | | | | |

| TGG | TGT | CAT | ATT | AAA | GGG | AAA | GTT | CCA | TTA | AAT | ACA | AGT | AAA | 1764 |
|---|---|---|---|---|---|---|---|---|---|---|---|---|---|---|
| Trp | Cys | His | Ile | Lys | Gly | Lys | Val | Pro | Leu | Asn | Thr | Ser | Lys | |
| 575 | | | | | 580 | | | | | 585 | | | | |

| GAC | TAT | GCA | TCA | GAA | GTA | AGT | TCA | TAC | ACT | AAG | GGC | TTA | GGC | 1806 |
|---|---|---|---|---|---|---|---|---|---|---|---|---|---|---|
| Asp | Tyr | Ala | Ser | Glu | Val | Ser | Ser | Tyr | Thr | Lys | Gly | Leu | Gly | |
| | | 590 | | | | | 595 | | | | | 600 | | |

| ATT | TTT | ATG | GTT | AAG | CCA | TGC | GGG | TAT | CAA | ATA | ACA | AAA | GGC | 1848 |
|---|---|---|---|---|---|---|---|---|---|---|---|---|---|---|
| Ile | Phe | Met | Val | Lys | Pro | Cys | Gly | Tyr | Gln | Ile | Thr | Lys | Gly | |
| | | 605 | | | | | 610 | | | | | 615 | | |

| GGT | TAT | TCT | GAT | AAT | ATC | CGC | ATG | AAC | GAA | AAA | GAT | AAA | CTT | 1890 |
|---|---|---|---|---|---|---|---|---|---|---|---|---|---|---|
| Gly | Tyr | Ser | Asp | Asn | Ile | Arg | Met | Asn | Glu | Lys | Asp | Lys | Leu | |
| | | | 620 | | | | | 625 | | | | | 630 | |

| TTA | TTC | ATG | TTC | CAA | AAA | TCA | ATG | TCA | TCA | AAA | TAA | | | 1926 |
|---|---|---|---|---|---|---|---|---|---|---|---|---|---|---|
| Leu | Phe | Met | Phe | Gln | Lys | Ser | Met | Ser | Ser | Lys | | | | |
| | | | | 635 | | | | | 640 | | | | | |